(12) United States Patent
Murakata et al.

(10) Patent No.: US 9,133,174 B2
(45) Date of Patent: Sep. 15, 2015

(54) METHOD FOR PRODUCING COUMARIN DERIVATIVE

(75) Inventors: Masatoshi Murakata, Tokyo (JP); Takuma Ikeda, Tokyo (JP); Takahiro Ichige, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/342,629

(22) PCT Filed: Sep. 5, 2012

(86) PCT No.: PCT/JP2012/072645
§ 371 (c)(1),
(2), (4) Date: Apr. 4, 2014

(87) PCT Pub. No.: WO2013/035754
PCT Pub. Date: Mar. 14, 2013

(65) Prior Publication Data
US 2014/0213786 A1    Jul. 31, 2014

(30) Foreign Application Priority Data
Sep. 5, 2011    (JP) ................. P2011-193308

(51) Int. Cl.
*C07D 213/75* (2006.01)
*C07D 405/14* (2006.01)
*C07D 405/06* (2006.01)

(52) U.S. Cl.
CPC ............ *C07D 405/14* (2013.01); *C07D 213/75* (2013.01); *C07D 405/06* (2013.01)

(58) Field of Classification Search
CPC .......................... C07D 213/75; C07D 405/14
See application file for complete search history.

(56) References Cited

U.S. PATENT DOCUMENTS

| 2010/0004233 A1 | 1/2010 | Iikura et al. |
| 2011/0009398 A1 | 1/2011 | Sakai et al. |

FOREIGN PATENT DOCUMENTS

| DE | 10 2006 037399 A1 | 2/2008 |
| EP | 0341961 A2 | 11/1989 |
| EP | 2172198 A1 | 4/2010 |
| JP | H02-036145 A | 2/1990 |
| WO | 02/08217 A2 | 1/2002 |
| WO | 2007/089512 A1 | 8/2007 |
| WO | 2007/091736 A1 | 8/2007 |
| WO | 2009/014100 A1 | 1/2009 |

OTHER PUBLICATIONS

Stanchev et al., "Synthesis, computational study and cytotoxic activity of new 4-hydroxycoumarin derivatives," European Journal of Medicinal Chemistry, 43: 694-706 (2008).
Stanchev et al., "Synthesis and Inhibiting Activity of Some 4-Hydroxycoumarin Derivatives on HIV-1 Protease," International Scholarly Research Network, ISRN Pharmaceutics, 2011: 9 pages (2011).
International Search Report issued in corresponding International Patent Application No. PCT/JP2012/072645 dated Nov. 20, 2012.
International Preliminary Report on Patentability issued in corresponding International Patent Application No. PCT/JP2012/072645 dated Mar. 20, 2014.
Extended European Search Report issued in counterpart European Patent Application No. 12829853.6 dated Mar. 5, 2015.
Frey et al., "Practical routes toward the synthesis of 2-halo- and 2-alkylamino-4-pyridinecarboxaldehydes," Tetrahedron Letters, 42: 6815-6818 (2001).

*Primary Examiner* — Bruck Kifle
(74) *Attorney, Agent, or Firm* — Morgan, Lewis & Bockius LLP

(57) ABSTRACT

The present invention provides a novel method for producing a compound represented by general formula (VII) below or a pharmaceutically acceptable salt thereof or a synthetic intermediate thereof:

(VII)

wherein $R^2$ represents a hydrogen atom or a halogen atom, $R^c$ represents a $C_{1-6}$ alkyl group, X represents a group selected from a heteroaryl group etc., $R^{11}$ represents an atom or group selected from a hydrogen atom, a halogen atom, a $C_{1-6}$ alkyl group, etc., $R^{16}$ and $R^{17}$ each independently represent an atom or group selected from a hydrogen atom, a $C_{1-6}$ alkyl group, etc., and $R^{15}$ represents a hydrogen atom or a $C_{1-6}$ alkyl group.

12 Claims, No Drawings

METHOD FOR PRODUCING COUMARIN DERIVATIVE

TECHNICAL FIELD

The present invention relates to a method for producing a coumarin derivative.

BACKGROUND ART

A compound represented by general formula (VII):

[Chemical Formula 1]

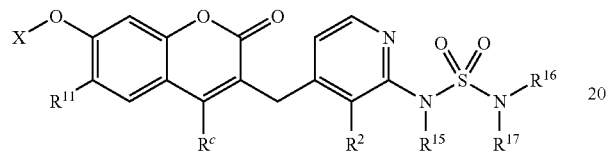

(VII)

[wherein $R^2$ represents a hydrogen atom or a halogen atom, $R^c$ represents a $C_{1-6}$ alkyl group, X represents a heteroaryl group or $R^{13}R^{14}NCO—$, $R^{11}$ represents a hydrogen atom, a halogen atom, a cyano group, a $C_{1-6}$ alkyl group, a $C_{2-7}$ alkenyl group, a carbamoyl group or a $C_{2-7}$ alkynyl group (where the $C_{2-7}$ alkynyl group may optionally be substituted with a $C_{1-4}$ acyl group), $R^{13}$, $R^{14}$, $R^{16}$ and $R^{17}$ each independently represent a hydrogen atom, a $C_{1-6}$ alkoxy group, a $C_{3-8}$ cycloalkyl group or a $C_{1-6}$ alkyl group (where the $C_{1-6}$ alkyl group may optionally be substituted with a cyano group, a halogen atom, a hydroxy group, a $C_{1-6}$ alkoxy group or $—NR^{23}R^{24}$) the combination of $R^{13}$ and $R^{14}$ and the combination of $R^{16}$ and $R^{17}$ may each independently, together with the nitrogen atom to which they are bonded, optionally form a 4- to 6-membered heterocyclic group having at least one nitrogen atom, and $R^{15}$, $R^{23}$ and $R^{24}$ each independently represent a hydrogen atom or a $C_{1-6}$ alkyl group]
or a pharmaceutically acceptable salt thereof (the compound or salt being also referred to hereunder as a "coumarin derivative of general formula (VII)") is known to have pharmacological activity such as antitumor activity (see Patent document 1 or 2).

A method for producing a coumarin derivative of general formula (VII) is disclosed in Patent document 1 or 2. Patent document 1 or 2 discloses a method represented by the scheme below [In the scheme, DMF represents N,N-dimethylformamide, TBS represents a tert-butyldimethylsilyl group, dba represents dibenzylideneacetone, and BINAP represents 2,2'-bis(diphenylphosphino)-1,1'-binaphthyl. Also, the numerical values (%) and "quant." given below some structural formulas indicate the yields of the respective compounds], for example (see the manufacturing example for "compound 1j-2-16-2K" in Patent document 1 or 2).

[Chemical Formula 2]

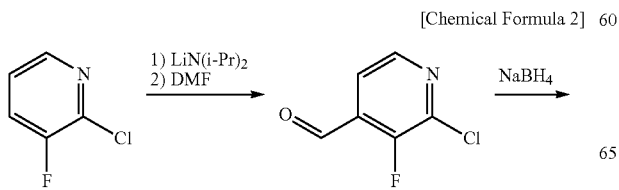

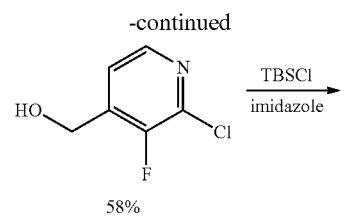
58%

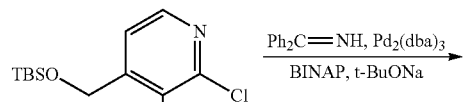
93%

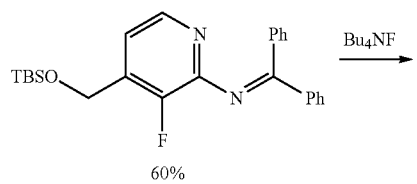
60%

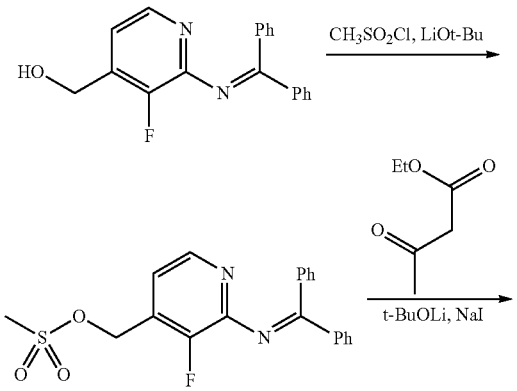

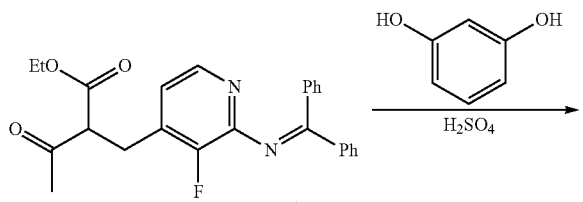
quant.

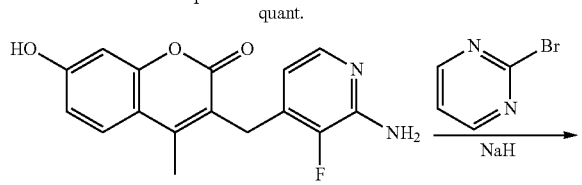

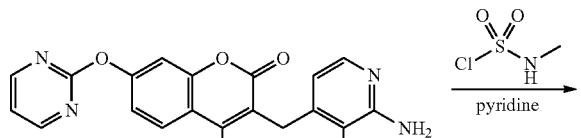

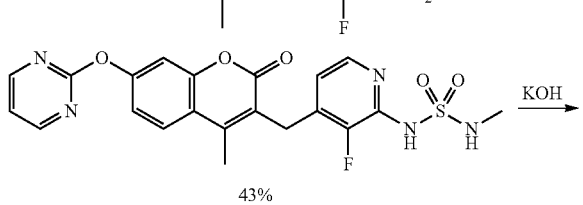
43%

-continued

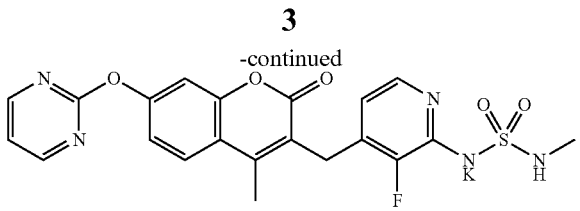

CITATION LIST

Patent Literature

Patent document 1: WO 2007/091736
Patent document 2: WO 2009/014100

SUMMARY OF INVENTION

Technical Problem

A coumarin derivative of general formula (VII) can be produced by the method disclosed in Patent document 1 or 2, but in the method disclosed in Patent document 1 or 2, it is necessary to perform steps of introduction and removal of a protecting group for the hydroxy group after the formylation and reduction reactions in order to suppress unintended reactions. Also, during the formylation reaction, cryogenic conditions (e.g., −95° C. to −65° C.) are necessary from the viewpoint of reaction control. Furthermore, in the alkylation reaction (7th step of the scheme shown above), it is preferred to use an excess of ethyl acetoacetate from the viewpoint of efficient synthesis, but this requires a cumbersome procedure for removal of the residual reagent.

The present invention has been made in light of such circumstances. It is an object of the present invention to provide a method for efficiently producing a coumarin derivative of general formula (VII) or a synthetic intermediate thereof by a simple process.

Solution to Problem

The present invention provides a method for producing a compound represented by general formula (VI):

[Chemical Formula 3]

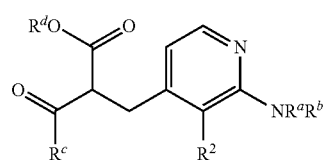

(VI)

[wherein $R^2$ represents a hydrogen atom or a halogen atom, $R^a$ and $R^b$ each independently represent a hydrogen atom or an amino protecting group, or $R^a$ and $R^b$ together may optionally form an amino protecting group, and $R^c$ and $R^d$ each independently represent a $C_{1-6}$ alkyl group], the method comprising steps A to D described below.

The present invention also provides a method for producing a compound represented by general formula (VII):

[Chemical Formula 4]

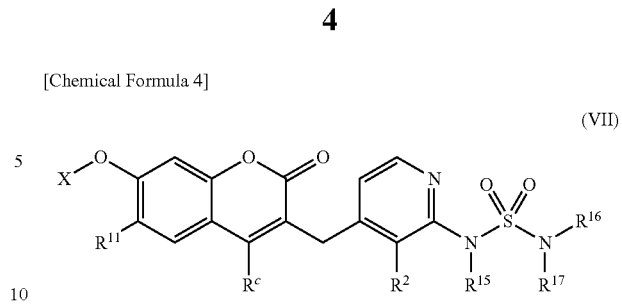

(VII)

[wherein $R^2$ and $R^c$ have the same definitions as above, X represents a heteroaryl group or $R^{13}R^{14}NCO-$, $R^{11}$ represents a hydrogen atom, a halogen atom, a cyano group, a $C_{1-6}$ alkyl group, a $C_{2-7}$ alkenyl group, a carbamoyl group or a $C_{2-7}$ alkynyl group (where the $C_{2-7}$ alkynyl group may optionally be substituted with a $C_{1-4}$ acyl group), $R^{13}$, $R^{14}$, $R^{16}$ and $R^{17}$ each independently represent a hydrogen atom, a $C_{1-6}$ alkoxy group, a $C_{3-8}$ cycloalkyl group or a $C_{1-6}$ alkyl group (where the $C_{1-6}$ alkyl group may optionally be substituted with a cyano group, a halogen atom, a hydroxy group, a $C_{1-6}$ alkoxy group or $-NR^{23}R^{24}$), or the combination of $R^{13}$ and $R^{14}$ and the combination of $R^{16}$ and $R^{17}$ may each independently, together with the nitrogen atom to which they are bonded, optionally form a 4- to 6-membered heterocyclic group having at least one nitrogen atom, and $R^{15}$, $R^{23}$ and $R^{24}$ each independently represent a hydrogen atom or a $C_{1-6}$ alkyl group]
or a pharmaceutically acceptable salt thereof, the method comprising steps A to D described below.

Step A:
A step in which $R^aR^bNH$ [wherein $R^a$ and $R^b$ have the same definitions as above] is reacted with a compound represented by general formula (I):

[Chemical Formula 5]

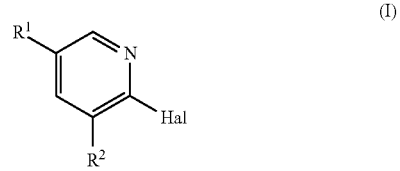

(I)

[wherein $R^1$ represents a hydrogen atom or a halogen atom, Hal represents a halogen atom, and $R^2$ has the same definition as above] to obtain a compound represented by general formula (II):

[Chemical Formula 6]

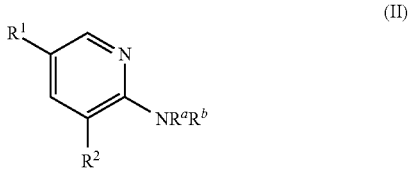

(II)

[wherein $R^1$, $R^2$, $R^a$ and $R^b$ have the same definitions as above].
Step B:
A step in which the compound represented by general formula (II) is reacted with a base and a formylating agent to obtain a compound represented by general formula (III):

[Chemical Formula 7]

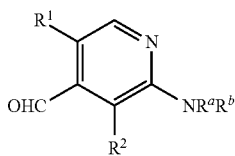

(III)

[wherein $R^1$, $R^2$, $R^a$ and $R^b$ have the same definitions as above].

Step C:

A step in which the compound represented by general formula (III) is reacted with a compound represented by general formula (IV):

[Chemical Formula 8]

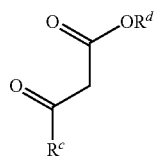

(IV)

[wherein $R^c$ and $R^d$ have the same definitions as above] to obtain a compound represented by general formula (V):

[Chemical Formula 9]

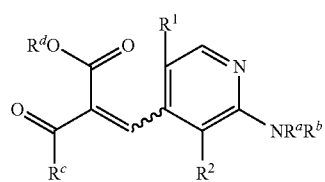

(V)

[wherein $R^1$, $R^2$, $R^a$, $R^b$, $R^c$ and $R^d$ have the same definitions as above].

Step D:

A step in which the compound represented by general formula (V) is subjected to (a) reduction of double bond (when $R^1$ is a hydrogen atom), or (b) reduction of double bond and hydrogenolysis of $R^1$ (when $R^1$ is a halogen atom), to obtain a compound represented by general formula (VI):

[Chemical Formula 10]

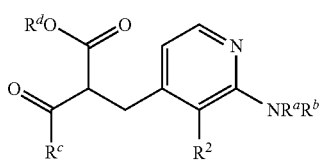

(VI)

[wherein $R^2$, $R^a$, $R^b$, $R^c$ and $R^d$ have the same definitions as above].

A compound of general formula (VI) is a synthetic intermediate of a coumarin derivative of general formula (VII), and the method of the present invention is a novel method for production of a coumarin derivative of general formula (VII) or a synthetic intermediate thereof.

Since the method of the present invention does not include a step of conversion of a formyl group to a hydroxy group after the formylation reaction, it is not necessary to perform steps of introduction and removal of a protecting group. Also, it is not necessary to perform the formylation reaction under cryogenic conditions. Also, the halogen atom can be converted to a nitrogen-containing substituent (amino group or protected amino group) without using a palladium catalyst and phosphine ligand. Also, in the alkylation reaction (step C), it is not necessary to use an excessive amount of an alkylating reagent (compound of general formula (IV)), which requires a cumbersome procedure for removal. Furthermore, the method of the present invention allows steps C and D to be performed continuously in one pot. According to the method of the present invention, therefore, it is possible to synthesize a compound of general formula (VI) or a coumarin derivative of general formula (VII) by fewer steps than conventional methods. Moreover, according to the method of the present invention, it is possible to efficiently produce a coumarin derivative of general formula (VII) or a synthetic intermediate thereof by a simple process.

The method of the present invention for producing a compound represented by general formula (VI) may consist of steps A to D described above.

The method of the present invention for producing a compound represented by general formula (VII) or a pharmaceutically acceptable salt thereof may further comprise steps E to G described below.

Step E:

A step in which the compound represented by general formula (VI) is reacted with a compound represented by general formula (VIII):

[Chemical Formula 11]

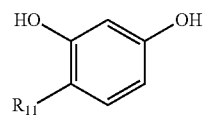

(VIII)

[wherein $R^{11}$ has the same definition as above] in the presence of an acid to obtain a compound represented by general formula (IX):

[Chemical Formula 12]

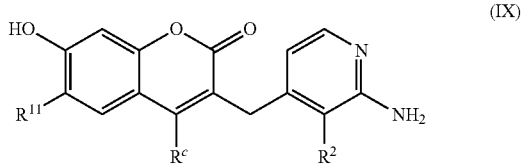

(IX)

[wherein $R^2$, $R^c$ and $R^{11}$ have the same definitions as above] or a pharmaceutically acceptable salt or acid adduct thereof.

Step F:

A step in which the compound represented by general formula (IX) or the pharmaceutically acceptable salt or acid adduct thereof is reacted with X—Y [wherein X has the same definition as above and Y represents a halogen atom] in the presence of a base to obtain a compound represented by general formula (X):

[Chemical Formula 13]

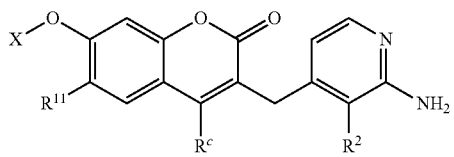

(X)

[wherein $R^2$, $R^c$, $R^{11}$ and X have the same definitions as above].

Step G:

A step in which the compound represented by general formula (X) is reacted with a compound represented by general formula (XI):

[Chemical Formula 14]

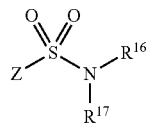

(XI)

[wherein $R^{16}$ and $R^{17}$ have the same definitions as above and Z represents a leaving group]

to obtain a compound represented by general formula (VII'):

[Chemical Formula 15]

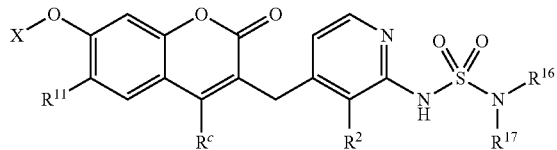

(VII')

[wherein $R^2$, $R^c$, $R^{11}$, X, $R^{16}$ and $R^{17}$ have the same definitions as above].

Advantageous Effects of Invention

According to the present invention, there is provided a method for efficiently producing a coumarin derivative of general formula (VII) or a synthetic intermediate thereof by a simple process.

DESCRIPTION OF EMBODIMENTS

Embodiments of the present invention will now be described.

The method of the present invention is a method for producing:

a compound represented by general formula (VI):

[Chemical Formula 16]

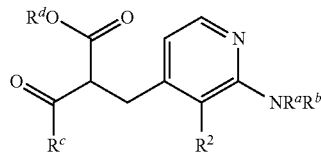

(VI)

[wherein $R^2$ represents a hydrogen atom or a halogen atom, $R^a$ and $R^b$ each independently represent a hydrogen atom or an amino protecting group, or $R^a$ and $R^b$ together may optionally form an amino protecting group, and $R^c$ and $R^d$ each independently represent a $C_{1-6}$ alkyl group], or a compound represented by general formula (VII):

[Chemical Formula 17]

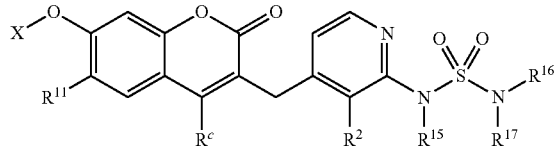

(VII)

[wherein $R^2$ and $R^c$ have the same definitions as above, X represents a heteroaryl group or $R^{13}R^{14}$NCO—, $R^{11}$ represents a hydrogen atom, a halogen atom, a cyano group, a $C_{1-6}$ alkyl group, a $C_{2-7}$ alkenyl group, a carbamoyl group or a $C_{2-7}$ alkynyl group (where the $C_{2-7}$ alkynyl group may optionally be substituted with a $C_{1-4}$ acyl group), $R^{13}$, $R^{14}$, $R^{16}$ and $R^{17}$ each independently represent a hydrogen atom, a $C_{1-6}$ alkoxy group, a $C_{3-8}$ cycloalkyl group or a $C_{1-6}$ alkyl group (where the $C_{1-6}$ alkyl group may optionally be substituted with a cyano group, a halogen atom, a hydroxy group, a $C_{1-6}$ alkoxy group or —$NR^{23}R^{24}$), or the combination of $R^{13}$ and $R^{14}$ and the combination of $R^{16}$ and $R^{17}$ may each independently, together with the nitrogen atom to which they are bonded, optionally form a 4- to 6-membered heterocyclic group having at least one nitrogen atom, and $R^{15}$, $R^{23}$ and $R^{24}$ each independently represent a hydrogen atom or a $C_{1-6}$ alkyl group]

or a pharmaceutically acceptable salt thereof, the method comprising steps A to D.

As used herein, the term "halogen atom" means a fluorine, chlorine, bromine or iodine atom.

The term "$C_{1-6}$ alkyl group" means a straight- or branched-chain alkyl group having 1 to 6 carbon atoms. Examples of the $C_{1-6}$ alkyl group include methyl, ethyl, n-propyl, i-propyl, n-butyl, sec-butyl, t-butyl, 1-methylpropyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

The term "$C_{2-7}$ alkenyl group" means a straight- or branched-chain alkenyl group having 2 to 7 carbon atoms. Examples of the $C_{2-7}$ alkenyl group include vinyl, allyl, 1-butenyl, 2-butenyl, 3-butenyl, pentenyl, pentadienyl, hexenyl, hexadienyl, heptenyl, heptadienyl, and heptatrienyl.

The term "$C_{2-7}$ alkynyl group" means a straight- or branched-chain alkynyl group having 2 to 7 carbon atoms.

Examples of the $C_{2-7}$ alkynyl group include ethynyl, 1-propynyl, 2-propynyl, 1-butynyl, 2-butynyl, 3-butynyl, pentynyl, pentadiynyl, hexynyl, hexadiynyl, heptynyl, heptadiynyl, and heptatriynyl.

The term "$C_{1-4}$ acyl group" means an acyl group having 1 to 4 carbon atoms. Examples of the $C_{1-4}$ acyl group include formyl, acetyl, n-propionyl, i-propionyl, butyryl, and sec-butyryl (isobutyryl).

The term "$C_{1-6}$ alkoxy group" means an alkyloxy group having, as the alkyl moiety, a straight- or branched-chain alkyl group having 1 to 6 carbon atoms. Examples of the $C_{1-6}$ alkoxy group include methoxy, ethoxy, n-propoxy, i-propoxy, n-butoxy, s-butoxy, t-butoxy, pentoxy, and hexoxy.

The term "$C_{3-8}$ cycloalkyl group" means a 3- to 8-membered cyclic alkyl group (where the cyclic alkyl group may optionally be substituted, on an atom of the ring, with a straight- or branched-chain alkyl group having 1 to 3 carbon atoms). Examples of the unsubstituted $C_{3-8}$ cycloalkyl group include cyclopropyl, cyclobutyl, cyclopentyl, cyclohexyl, cycloheptyl, and cyclooctyl. Examples of the substituted $C_{3-8}$ cycloalkyl group include methylcyclopropyl, ethylcyclopropyl, dimethylcyclopropyl, trimethylcyclopropyl, diethylcyclopropyl, ethyl methylcyclopropyl, dimethylethylcyclopropyl, diethylmethylcyclopropyl, methylcyclobutyl, ethylcyclobutyl, di methylcyclobutyl, trimethylcyclobutyl, tetramethylcyclobutyl, diethylcyclobutyl, ethylmethylcyclobutyl, dimethylethylcyclobutyl, methylcyclopentyl, ethylcyclopentyl, dimethylcyclopentyl, trimethylcyclopentyl, ethyl methylcyclopentyl, methylcyclohexyl, ethylcyclohexyl, dimethylcyclohexyl, and methylcycloheptyl.

The term "heteroaryl group" means a 5- to 10-membered aromatic heterocyclic group having at least one heteroatom selected from oxygen, nitrogen and sulfur atoms (where the aromatic heterocyclic group may optionally be substituted on an atom of the ring). Examples of the heteroaryl group include furyl, thienyl, pyrrolyl, imidazolyl, pyrazolyl, oxazolyl, isooxazolyl, thiazolyl, isothiazolyl, oxadiazolyl, thiadiazolyl, triazolyl, tetrazolyl, pyridyl, pyrimidinyl, pyrazinyl, pyridazinyl, triazinyl, benzofuranyl, benzothienyl, benzothiadiazolyl, benzothiazolyl, benzooxazolyl, benzooxadiazolyl, benzoimidazolyl, indolyl, isoindolyl, indazolyl, quinolyl, isoquinolyl, cinnolinyl, quinazolinyl, quinoxalinyl, indolizinyl, and imidazopyridyl.

The heteroaryl group may optionally be substituted with, for example, a halogen atom, a $C_{1-6}$ alkyl group, a $C_{1-6}$ alkoxy group, a cyano group, an amino group, a carbamoyl group, a nitro group, a carboxy group, a $C_{2-7}$ alkenyl group or a $C_{2-7}$ alkynyl group on an atom of the ring.

The term "4- to 6-membered heterocyclic group having at least one nitrogen atom" means a 4- to 6-membered saturated or unsaturated cyclic group having at least one nitrogen atom (where the saturated or unsaturated cyclic group may optionally have an oxygen atom and/or sulfur atom, may optionally be fused with a benzene ring, and may optionally be substituted on an atom of the ring). Examples of the 4- to 6-membered heterocyclic group having at least one nitrogen atom include azetidinyl, pyrrolidinyl, piperidinyl, piperazinyl, pyrrolyl, dihydropyrrolyl, imidazolyl, imidazolinyl, imidazolidinyl, pyrazolyl, pyrazolinyl, pyridazolidinyl, oxazolinyl, oxazolidinyl, morpholinyl, thiomorpholinyl, pyridinyl, dihydropyridinyl, pyrazinyl, pyrimidinyl, and pyridazinyl.

The 4- to 6-membered heterocyclic group having at least one nitrogen atom may optionally be substituted with, for example, a halogen atom, a $C_{1-6}$ alkyl group, a $C_{1-6}$ alkoxy group, a cyano group, an amino group, a carbamoyl group, a nitro group, a carboxy group, a $C_{2-7}$ alkenyl group or a $C_{2-7}$ alkynyl group on an atom of the ring.

Step A:

Step A is a step in which $R^a R^b NH$ [wherein $R^a$ and $R^b$ have the same definitions as above] is reacted with a compound represented by general formula (I):

[Chemical Formula 18]

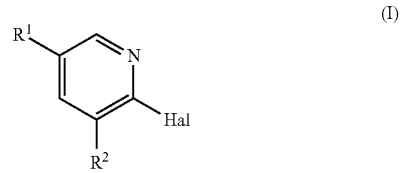

(I)

[wherein $R^1$ represents a hydrogen atom or a halogen atom, Hal represents a halogen atom, and $R^2$ has the same definition as above] to obtain a compound represented by general formula (II):

[Chemical Formula 19]

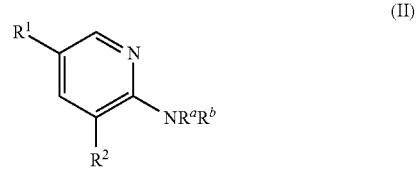

(II)

[wherein $R^1$, $R^2$, $R^a$ and $R^b$ have the same definitions as above].

When one of $R^a$ and $R^b$ is a hydrogen atom and the other is an amino protecting group, the amino protecting group may be, for example, a $C_{1-6}$ alkylcarbonyl group (e.g., acetyl, propionyl, butyryl, isobutyryl, valeryl, isovaleryl, or pivaloyl), a carbamoyl group, a $C_{1-6}$ alkoxycarbonyl group (e.g., methoxycarbonyl, ethoxycarbonyl, isopropyloxycarbonyl, or sec-butoxycarbonyl), a substituted silyl group (e.g., trimethylsilyl, triethylsilyl, triisopropylsilyl, t-butyldimethylsilyl, or t-butyldiphenylsilyl), an allyl group, or an aralkyl group (where the aryl group (e.g., phenyl, 1-naphthyl, or 2-naphthyl) in the aralkyl group may optionally be substituted with a $C_{1-6}$ alkyl group, a $C_{1-6}$ alkoxy group, a nitro group or a halogen atom).

When both $R^a$ and $R^b$ are amino protecting groups, the amino protecting group may be, for example, a $C_{1-6}$ alkylcarbonyl group (e.g., acetyl, propionyl, butyryl, isobutyryl, valeryl, isovaleryl, or pivaloyl), a substituted oxycarbonyl group (e.g., methoxycarbonyl, ethoxycarbonyl, t-butoxycarbonyl, benzyloxycarbonyl, or 4-methoxybenzyloxycarbonyl), a carbamoyl group, a substituted silyl group (e.g., trimethylsilyl, triethylsilyl, triisopropylsilyl, t-butyldimethylsilyl, or t-butyldiphenylsilyl), an aralkyl group (where the aryl group (e.g., phenyl, 1-naphthyl, or 2-naphthyl) in the aralkyl group may optionally be substituted with a $C_{1-6}$ alkyl group, a $C_{1-6}$ alkoxy group, a nitro group or a halogen atom), or an allyl group.

The case where $R^a$ and $R^b$ together form an amino protecting group may be, for example, a case where a divalent substituent (e.g., 1,1-dimethylthiomethylene, benzylidene, p-methoxybenzylidene, diphenylmethylene, [(2-pyridyl)mesityl]methylene, N,N-dimethylaminomethylene, isopropylidene, p-nitrobenzylidene, (5-chloro-2-hydroxyphenyl)phenylmethylene, or cyclohexylidene) forms an imino group together with the nitrogen atom of an amino group.

It is preferred that one of $R^a$ and $R^b$ is a hydrogen atom and the other is an amino protecting group, or that both are amino protecting groups; it is more preferred that one is a hydrogen atom and the other is an amino protecting group; it is further preferred that one is a hydrogen atom and the other is a $C_{1-6}$ alkylcarbonyl group; and it is particularly preferred that one is a hydrogen atom and the other is an acetyl group.

When $R^1$ is a halogen atom, it is preferably a chlorine atom, a bromine atom or an iodine atom, and particularly preferably a chlorine atom.

It is preferred that both $R^1$ and $R^2$ are halogen atoms, that $R^1$ is a hydrogen atom and $R^2$ is a halogen atom, or that $R^1$ is a halogen atom and $R^2$ is a hydrogen atom; and it is particularly preferred that both $R^1$ and $R^2$ are halogen atoms. When both $R^1$ and $R^2$ are halogen atoms, they are preferably different, and it is particularly preferred that $R^1$ is a chlorine atom and $R^2$ is a fluorine atom.

A compound of general formula (I) can be synthesized based on a method disclosed in published literature. For example, 5-chloro-2,3-difluoropyridine is disclosed in Synthetic Communications, 34, 4301-4311, 2004 and can be synthesized by the method disclosed in that publication. A commercially available product may also be used as a compound of general formula (I). For example, the product marketed by Tokyo Chemical Industry Co., Ltd. (product code: C2113) may be purchased.

Examples of reaction solvents which may be used in step A include ether solvents (e.g., tetrahydrofuran, methyltetrahydrofuran, diethyl ether, t-butyl methyl ether, diisopropyl ether, cyclopentyl methyl ether, and 1,2-dimethoxyethane), hydrocarbon solvents (e.g., hexane, heptane, benzene, and toluene), amide solvents (e.g., N,N-dimethylformamide, N,N-dimethylacetamide, and N-methylpyrrolidone), and mixtures of (two or more of) them.

The reaction can be performed by stirring the reaction mixture at an appropriate temperature (e.g., –50° C. to 150° C.) for a certain period of time (e.g., 0.1 hours to 5 hours).

It is preferred that $R^aR^bNH$ is reacted with a base before being reacted with a compound of general formula (I). The base is preferably sodium hexamethyldisilazide or sodium hydride, for example. Examples of reaction solvents which may be used include ether solvents (e.g., tetrahydrofuran, methyltetrahydrofuran, diethyl ether, t-butyl methyl ether, diisopropyl ether, cyclopentyl methyl ether, and 1,2-dimethoxyethane), hydrocarbon solvents (e.g., hexane, heptane, benzene, and toluene), amide solvents (e.g., N,N-dimethylformamide, N,N-dimethylacetamide, and N-methylpyrrolidone), and mixtures of (two or more of) them. The reaction can be performed by stirring the reaction mixture at an appropriate temperature (e.g., –30° C. to 80° C.) for a certain period of time (e.g., 0.1 hours to 3 hours).

The mixture obtained upon completion of the reaction of step A may be directly supplied to step B, but generally it is subjected to post-treatment such as washing or extraction. It may also be further subjected to isolation (e.g., concentration or crystallization) or purification (e.g., recrystallization or column chromatography) before being supplied to step B.

Step B:

Step B is a step in which the compound represented by general formula (II) is reacted with a base and a formylating agent to obtain a compound represented by general formula (III):

[Chemical Formula 20]

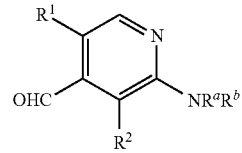

[wherein R', $R^2$, $R^a$ and $R^b$ have the same definitions as above].

The combination of the base and the formylating agent is, for example, preferably a combination of lithium hexamethyldisilazide and N,N-dimethylformamide or a combination of lithium hexamethyldisilazide and 4-formylmorpholine, and particularly preferably a combination of lithium hexamethyldisilazide and 4-formylmorpholine.

When the compound of general formula (II) is to be reacted with a base and a formylating agent, the compound of general formula (II) may be first mixed with the base and then mixed with the formylating agent, or the compound of general formula (II) may be first mixed with the formylating agent and then mixed with the base. When the base itself is unstable or the product obtained from the reaction of the compound of general formula (II) with the base is unstable, it is preferred that the compound is first mixed with the formylating agent and then the resulting mixture is mixed with the base.

Examples of solvents which may be used when the compound of general formula (II) is to be reacted with a base include ether solvents (e.g., tetrahydrofuran, methyltetrahydrofuran, diethyl ether, t-butyl methyl ether, diisopropyl ether, cyclopentyl methyl ether, and 1,2-dimethoxyethane), hydrocarbon solvents (e.g., hexane, heptane, benzene, and toluene), amide solvents (e.g., N,N-dimethylformamide, N,N-dimethylacetamide, and N-methylpyrrolidone), and mixtures of (two or more of) them. The reaction can be performed by stirring the reaction mixture at an appropriate temperature (e.g., –100° C. to 50° C.) for a certain period of time (e.g., 0.1 hours to 10 hours).

Examples of solvents which may be used when the compound of general formula (II) is to be reacted with a formylating agent include ether solvents (e.g., tetrahydrofuran, methyltetrahydrofuran, diethyl ether, t-butyl methyl ether, diisopropyl ether, cyclopentyl methyl ether, and 1,2-dimethoxyethane), hydrocarbon solvents (e.g., hexane, heptane, benzene, and toluene), amide solvents (e.g., N,N-dimethylformamide, N,N-dimethylacetamide, and N-methylpyrrolidone), and mixtures of (two or more of) them. The reaction can be performed by stirring the reaction mixture at an appropriate temperature (e.g., –100° C. to 50° C.) for a certain period of time (e.g., 0.1 hours to 10 hours). The reaction temperature is, for example, preferably –100° C. to 50° C., more preferably –50° C. to 0° C., and even more preferably –30° C. to –10° C.

The mixture obtained upon completion of the reaction of step B may be directly supplied to step C or may be subjected to post-treatment such as washing or extraction. It may also be subjected to post-treatment and further subjected to isolation (e.g., concentration or crystallization) or purification (e.g., recrystallization or column chromatography) before being supplied to step C, but in that case, it is preferably supplied to step C upon completion of the isolation.

Steps C and D:

Step C is a step in which the compound represented by general formula (III) is reacted with a compound represented by general formula (IV):

[Chemical Formula 21]

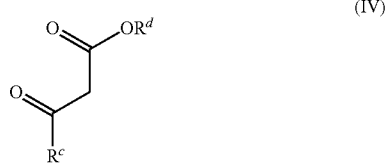

(IV)

[wherein $R^c$ and $R^d$ have the same definitions as above] to obtain a compound represented by general formula (V):

[Chemical Formula 22]

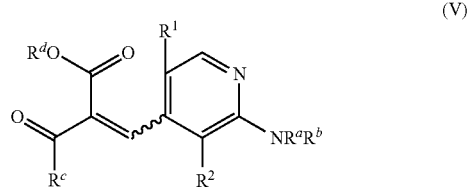

(V)

[wherein $R^1$, $R^2$, $R^a$, $R^b$, $R^c$ and $R^d$ have the same definitions as above].

Step D is a step in which the compound represented by general formula (V) is subjected to (a) reduction of double bond (when $R^1$ is a hydrogen atom), or (b) reduction of double bond and hydrogenolysis of $R^1$ (when $R^1$ is a halogen atom), to obtain a compound represented by general formula (VI):

[Chemical Formula 23]

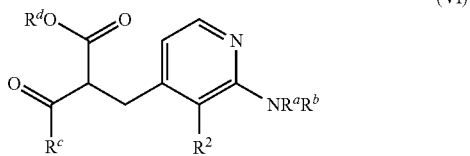

(VI)

[wherein $R^2$, $R^a$, $R^b$, $R^c$ and $R^d$ have the same definitions as above].

In step C, from the viewpoint of improving the product yield and/or reducing the reaction time, the reaction is preferably performed in the presence of a base or an acid, particularly preferably in the presence of both a base and an acid. Preferred examples of the base include amines such as ammonia, primary amines (e.g., methylamine, ethylamine, propylamine, and cyclohexylamine), secondary amines (e.g., dimethylamine, diethylamine, dipropylamine, dicyclohexylamine, ethylisopropylamine, pyrrolidine, piperidine, piperazine, and morpholine), tertiary amines (e.g., triethylamine, N-methylmorpholine, ethyldiisopropylamine, DBU, and DABCO), diamines (e.g., ethylenediamine, propylenediamine, aminoethylpiperidine, and aminoethylmorpholine) and guanidine, with piperidine being particularly preferred. Examples of bases which may be used also include derivatives of amino acids (e.g., alanine, β-alanine, histidine, proline, lysine, and arginine) (examples of such derivatives including histidine methyl ester, proline ethyl ester, lysine ethyl ester, arginine ethyl ester, dipeptides, and tripeptides), derivatives (e.g., esters) of aminophosphoric acids (e.g., 1-aminoethylphosphoric acid and 2-aminoethylphosphoric acid), derivatives (e.g., esters) of carboxyalkylphosphines (e.g., carboxymethylphosphine and carboxyethylphosphine), and derivatives (e.g., esters) of carboxyalkylphosphine oxides (e.g., carboxymethylphosphine oxide and carboxyethylphosphine oxide). Preferred examples of the acid include carboxylic acids such as acetic acid, oxalic acid, maleic acid, fumaric acid, succinic acid, malonic acid, citric acid, benzoic acid, salicylic acid, tartaric acid, propionic acid, butyric acid, isobutyric acid, valeric acid, isovaleric acid and pivalic acid, with acetic acid being particularly preferred. When both a base and an acid are to be used, a compound having both a basic functional group and an acidic functional group can also be used. Examples of such compounds include amino acids (e.g., alanine, β-alanine, histidine, proline, lysine, and arginine) or salts thereof and aminophosphoric acids (e.g., 1-aminoethylphosphoric acid and 2-aminoethylphosphoric acid) or salts thereof. Examples of such compounds also include carboxyalkylphosphines (e.g., carboxymethylphosphine and carboxyethylphosphine), carboxyalkylphosphine oxides (e.g., carboxymethylphosphine oxide and carboxyethylphosphine oxide), or salts thereof. When both a base and an acid are to be used, a salt of a compound having a basic functional group (examples of such compounds including bases mentioned above) and a compound having an acidic functional group (examples of such compounds including acids mentioned above) can also be used. Examples of such salts include oxalate of ammonia, acetate of ethylamine, hemimaleate of propylamine, benzoate of cyclohexylamine, hemitartarate of N-methylmorpholine, diacetate of ethylenediamine (ethylenediamine diacetate), dipropionate of ethylenediamine, diacetate of propylenediamine, and diacetate of aminoethylpiperidine. When both a base and an acid are to be used, the combination is preferably a combination of piperidine and acetic acid, for example. When both a base and an acid are to be used, it is also preferred to use lysine, histidine, or ethylenediamine diacetate (particularly ethylenediamine diacetate).

The reaction of step C can be performed by stirring the reaction mixture at an appropriate temperature (e.g., 0° C. to 80° C.) for a certain period of time (e.g., 0.1 hours to 30 hours).

The reduction of double bond in step D may be heterogeneous reduction or homogeneous catalytic reduction, for example. The heterogeneous reduction may be, for example, reduction by hydrogen-platinum dioxide, hydrogen-platinum/carbon, hydrogen-palladium/carbon, hydrogen-palladium hydroxide/carbon, hydrogen-palladium black, hydrogen-palladium/barium sulfate, hydrogen-Raney nickel, hydrogen-copper chromite, hydrogen-rhodium/carbon, hydrogen-rhodium/alumina, hydrogen-ruthenium dioxide, hydrogen-ruthenium/carbon, formic acid-palladium/carbon, formic acid-palladium hydroxide/carbon, or formic acid-palladium black. The homogeneous catalytic reduction may be, for example, catalytic reduction by hydrogen-chlorotris(triphenylphosphine)rhodium(I), hydrogen-chlorotris(tri-paratolylphosphine)rhodium(I), hydrogen-chlorotris(tri-parametheoxyphenylphosphine)rhodium(I), hydrogen-hydridocarbonyltris(triphenylphosphine)rhodium(I), hydrogen-rhodium(II) acetate, hydrogen-ruthenium(II) acetate, hydrogen-chlorohydridotris(triphenylphosphine)ruthenium(II), hydrogen-carboxylatehydridotris(triphenylphosphine)ruthenium(II), hydrogen-hydridocarbonyltris(triphenylphosphine)iridium(I), hydrogen-platinum(II)-tin chloride complex, hydrogen-pentacyanocobalt(II) complex, hydrogen-tricyanobipyridine cobalt(II) complex, hydrogen-bis(dimethylglyoximato)cobalt(II) complex, hydrogen-methyl benzoate-tricarbonylchromium complex, hydrogen-bis(tricarbonylcyclopentadienylchromium), hydrogen-pentacarbonyliron, hydrogen-bis(cyclopentadienyl)dicarbonyltitanium, hydrogen-hydridocarbonylcobalt complex, hydrogen-octacarbonyldicobalt, hydrogen-hydridocarbonylrhodium, hydrogen-chromium(III) acetylacetonate-triisobutylaluminum, hydrogen-cobalt(II) acetylacetonate-triisobutylaluminum, or hydrogen-nickel(II) 2-hexanoate-triethylaluminum. The reduction reaction can also be performed using a metal hydride reagent (e.g., sodium borohydride, lithium borohydride, sodium borohydride-pyridine complex, sodium borohydride-picoline complex, sodium borohydride-tetrahydrofuran complex, or triethylsilane). The reduction reaction can be performed by stirring the reaction mixture at atmospheric pressure or under pressure at an appropriate temperature (e.g., −100° C. to 50° C.) for a certain period of time (e.g., 0.1 hours to 20 hours).

The hydrogenolysis of $R^1$ in step D can be performed using an appropriate hydrogen source in the presence of a catalyst. The catalyst may be either a heterogeneous catalyst or a homogeneous catalyst. Examples of heterogeneous catalysts include platinum dioxide, platinum/carbon, palladium/carbon, palladium hydroxide/carbon, palladium black, and Raney nickel. Examples of homogeneous catalysts include chlorotris(triphenylphosphine)rhodium(I), chlorotris(triparatolylphosphine)rhodium(I), chlorotris(triparamethoxyphenylphosphine)rhodium(I), hydridocarbonyltris(triphenylphosphine)rhodium(I), rhodium(II) acetate, ruthenium (II) acetate, chlorohydridotris(triphenylphosphine)ruthenium(II), and carboxylatehydridotris(triphenylphosphine)ruthenium(II). Examples of hydrogen sources include hydrogen, formic acid, ammonium formate, sodium formate, formic acid-triethylamine, triethylsilane, tetramethyldisiloxane, and polymethylhydrosiloxane. The hydrogenolysis reaction can be performed by stirring the reaction mixture at atmospheric pressure or under pressure at an appropriate temperature (e.g., 0° C. to 100° C.) for a certain period of time (e.g., 0.1 hours to 20 hours).

When the reduction of double bond and the hydrogenolysis of $R^1$ are to be performed in step D, they may be performed simultaneously or in any order, but they are preferably performed simultaneously. When the two reactions are to be performed simultaneously, it is preferred from the viewpoint of efficiency that they are performed in a single reaction operation.

Preferred examples of reaction solvents which may be used in steps C and D include ether solvents (e.g., ether, tetrahydrofuran, dioxane, dimethoxyethane, cyclopentyl methyl ether, and methyl tert-butyl ether), aromatic hydrocarbon solvents (e.g., benzene, toluene, xylene, quinoline, and chlorobenzene), aliphatic hydrocarbon solvents (e.g., pentane, hexane, heptane, and octane), amide solvents (e.g., N,N-dimethylformamide, N,N-dimethylacetamide, and N-methylpyrrolidone), alcohol solvents (e.g., methanol, ethanol, trifluoroethanol, n-propanol, 2-propanol, n-butanol, sec-butanol, t-butanol, pentanol, hexanol, cyclopropanol, cyclobutanol, cyclopentanol, cyclohexanol, ethylene glycol, 1,3-propanediol, 1,4-butanediol, and 1,5-pentanediol), acetate ester solvents (e.g., methyl acetate, ethyl acetate, and isopropyl acetate), acetonitrile, and mixtures of (two or more of) those organic solvents, with 2,2,2-trifluoroethanol and acetonitrile being preferred and 2,2,2-trifluoroethanol being particularly preferred. Examples of mixtures of two or more of the organic solvents mentioned above include a mixed solvent of 2-propanol and toluene, a mixed solvent of methanol and benzene, a mixed solvent of ethanol and xylene, and a mixed solvent of n-propanol and chlorobenzene. Water may also be used, or a mixed solvent of water and an organic solvent mentioned above (the organic solvent being optionally a mixture of two or more of the organic solvents mentioned above) may be used.

As the reaction solvent in step C, a mixed solvent of water, an acetate ester solvent (e.g., methyl acetate, ethyl acetate, or isopropyl acetate) and an aromatic hydrocarbon solvent (e.g., benzene, toluene, xylene, quinoline, or chlorobenzene), for example, is also preferred. Ethyl acetate is particularly preferred as the acetate ester solvent, toluene is particularly preferred as the aromatic hydrocarbon solvent, and a mixture of water, ethyl acetate and toluene is particularly preferred as the mixed solvent. When a mixed solvent of water, an acetate ester solvent and an aromatic hydrocarbon solvent is to be used, the solvent composition (volume ratio of water, the acetate ester solvent and the aromatic hydrocarbon solvent) is, for example, preferably 3-5: 2-4: 4-6, more preferably 7-9: 5-7: 9-11, and even more preferably 11-13: 8-10: 14-16. The solvent compositions listed in Table 1-1 and Table 1-2 may also be mentioned as preferred examples of solvent compositions.

When a combination of piperidine and acetic acid is to be used as the base and the acid in step C, the reaction solvent is, for example, preferably an organic solvent mentioned above (which may optionally be a mixture of two or more of the organic solvents mentioned above), and it is particularly preferred that 2,2,2-trifluoroethanol is used alone. Also, when lysine, histidine or ethylenediamine diacetate is to be used as the base and the acid in step C, the reaction solvent is, for example, preferably a mixed solvent of water and an organic solvent mentioned above (the organic solvent being optionally a mixture of two or more of the organic solvents mentioned above), more preferably a mixed solvent of water, an acetate ester solvent (e.g., methyl acetate, ethyl acetate, or isopropyl acetate) and an aromatic hydrocarbon solvent (e.g., benzene, toluene, xylene, quinoline, or chlorobenzene), and particularly preferably a mixture of water, ethyl acetate and toluene.

As the reaction solvent in step D, a mixed solvent of an acetate ester solvent (e.g., methyl acetate, ethyl acetate, or isopropyl acetate), an aromatic hydrocarbon solvent (e.g., benzene, toluene, xylene, quinoline, or chlorobenzene) and an alcohol solvent (e.g., methanol, ethanol, trifluoroethanol, n-propanol, 2-propanol, n-butanol, sec-butanol, t-butanol, pentanol, hexanol, cyclopropanol, cyclobutanol, cyclopentanol, cyclohexanol, ethylene glycol, 1,3-propanediol, 1,4-butanediol, or 1,5-pentanediol), for example, is also preferred. Ethyl acetate is particularly preferred as the acetate ester solvent, toluene is particularly preferred as the aromatic hydrocarbon solvent, 2-propanol is particularly preferred as the alcohol solvent, and a mixture of ethyl acetate, toluene and 2-propanol is particularly preferred as the mixed solvent. When a mixed solvent of an acetate ester solvent, an aromatic hydrocarbon solvent and an alcohol solvent is to be used, the solvent composition (volume ratio of the acetate ester solvent, the aromatic hydrocarbon solvent and the alcohol solvent) is, for example, preferably 2-4: 4-6: 8-15, more preferably 5-7: 9-11: 20-26, and even more preferably 8-10: 14-16: 44-48.

The tables below (Table 1-1 and Table 1-2) show: preferred examples of the solvent composition and reaction temperature when a mixed solvent of water and an organic solvent mentioned above (the organic solvent being optionally a mixture of two or more of the organic solvents mentioned above) is to be used in step C or D; and preferred examples of the catalyst (base and/or acid) when a mixed solvent is to be used in step C. In the tables, "CPME" stands for cyclopentyl methyl ether and "MTBE" stands for methyl tert-butyl ether. Also, "room temperature" means a temperature of 15° C. to 25° C. The phosphate buffer (pH 6.5) may have the composition shown below, for example. The sodium citrate buffer (pH 5.1 or pH 4.3) may be, for example, one manufactured by Wako Pure Chemical Industries, Ltd (Catalog No.: 195-07285 or 198-07275).

Phosphate Buffer Composition:

Potassium dihydrogenphosphate: approximately 2.6% w/v

Sodium hydroxide: approximately 0.2% w/v

TABLE 1-1

| Base | Acid | Solvent composition (v/v/v) | Reaction temperature |
|---|---|---|---|
| Ethylenediamine | Acetic acid | Water/toluene/ethyl acetate (8/5/3) | 40° C. |
| Ethylenediamine | Acetic acid | Water/toluene/ethyl acetate (Water/organic solvent = 1/2) | 40° C. |
| Ethylenediamine | Acetic acid | Water/isopropyl acetate (1/1) | 40° C. |
| Ethylenediamine | Acetic acid | Water/CPME/isopropyl acetate (2/1/1) | 40° C. |
| Ethylenediamine | Acetic acid | Water/MTBE/isopropyl acetate (2/1/1) | 40° C. |
| Ethylenediamine | Acetic acid | Water/heptane/isopropyl acetate (2/0.1/1) | 40° C. |
| Ethylenediamine | Maleic acid | Water/toluene/ethyl acetate (8/5/3) | 40° C. |
| Ethylenediamine | Fumaric acid | Water/toluene/ethyl acetate (8/5/3) | 40° C. |
| Ethylenediamine | Malonic acid | Water/toluene/ethyl acetate (8/5/3) | 40° C. |
| Ethylenediamine | Succinic acid | Water/toluene/ethyl acetate (8/5/3) | 40° C. |
| 1,3-Diaminopropane | Acetic acid | Water/toluene/ethyl acetate (8/5/3) | 40° C. |
| 1,4-Diaminobutane | Acetic acid | Water/toluene/ethyl acetate (8/5/3) | 40° C. |
| $(NH_2C_2H_4)_2O$ | Acetic acid | Water/toluene/ethyl acetate (8/5/3) | 40° C. |
| $(NH_2C_2H_4)_3N$ | Acetic acid | Water/toluene/ethyl acetate (8/5/3) | 40° C. |
| $(NH_2C_2H_4)_2NH$ | Acetic acid | Water/toluene/ethyl acetate (8/5/3) | 40° C. |

TABLE 1-2

| Base and/or acid | Solvent composition (v/v/v) | Reaction temperature |
|---|---|---|
| 1-(3-Aminopropyl)imidazole | Sodium citrate buffer (pH 5.1)/toluene/ethyl acetate (8/5/3) | 40° C. |
| L-Histidine | Water/toluene/ethyl acetate (8/5/3) | 50° C. |
| L-Histidine | Water/toluene/ethyl acetate (8/5/3) | Room temperature |
| L-Histidine | Phosphate buffer (pH 6.5)/toluene/ethyl acetate (8/5/3) | 40° C. |
| L(+)-Lysine | Water/toluene/ethyl acetate (8/5/3) | 40° C. |
| L(+)-Lysine | Phosphate buffer (pH 6.5)/toluene/ethyl acetate (8/5/3) | Room temperature |

TABLE 1-2-continued

| Base and/or acid | Solvent composition (v/v/v) | Reaction temperature |
|---|---|---|
| L(+)-Lysine | Sodium citrate buffer (pH 5.1)/toluene/ethyl acetate (8/5/3) | 40° C. |
| β-Alanine sodium salt | Sodium citrate buffer (pH 5.1)/toluene/ethyl acetate (8/5/3) | 40° C. |
| β-Alanine sodium salt | Sodium citrate buffer (pH 4.3)/toluene/ethyl acetate (8/5/3) | 40° C. |
| 2-Aminoethylphosphonic acid monosodium salt | Water/toluene/ethyl acetate (8/5/3) | 40° C. |
| 2-Aminoethylphosphonic acid monosodium salt | Sodium citrate buffer (pH 5.1)/toluene/ethyl acetate (8/5/3) | 40° C. |
| 2-Aminoethylphosphonic acid monosodium salt | Sodium citrate buffer (pH 4.3)/toluene/ethyl acetate (8/5/3) | 40° C. |
| 2-Aminoethylphosphonic acid disodium salt | Sodium citrate buffer (pH 5.1)/toluene/ethyl acetate (8/5/3) | 40° C. |
| 2-Aminoethylphosphonic acid disodium salt | Sodium citrate buffer (pH 4.3)/toluene/ethyl acetate (8/5/3) | 40° C. |

The mixture obtained upon completion of the reaction of step C may be subjected to post-treatment such as washing or extraction, or isolation or purification before being supplied to step D, but it is preferred that the mixture is directly supplied to step D without such treatment. When steps C and D are to be performed continuously in one pot, the reaction solvent is preferably 2,2,2-trifluoroethanol, for example.

Also, when the reaction solvent used in step C is a mixed solvent of water, an acetate ester solvent and an aromatic hydrocarbon solvent (e.g., a mixture of water, ethyl acetate and toluene), it is preferred from the viewpoint of efficiency etc. that the aqueous layer is removed from the reaction mixture upon completion of the reaction of step C to obtain an organic layer, that an alcohol solvent (e.g., 2-propanol) is then added to the organic layer without washing, purification, etc., and that the resultant mixture is supplied to step D.

When the compound of general formula (VI) obtained in step D is to be further subjected to another reaction (e.g., the reaction of step E), the mixture obtained upon completion of the reaction of step D may be directly supplied to the subsequent step, but generally it is subjected to post-treatment such as washing or extraction. It may also be further subjected to isolation (e.g., concentration or crystallization) or purification (e.g., recrystallization or column chromatography) before being supplied to the subsequent step. It is preferred that the mixture obtained upon completion of the reaction is subjected to post-treatment (e.g., washing or extraction) and then to isolation (e.g., concentration or crystallization), and supplied to step E upon completion of the isolation.

Also, when the reaction solvent used in step D is a mixed solvent of an acetate ester solvent, an aromatic hydrocarbon solvent and an alcohol solvent (e.g., a mixture of ethyl acetate, toluene and 2-propanol), the mixture obtained upon completion of the reaction of step D may be supplied directly to the subsequent step (e.g., step E), or post-treatment such as filtration, washing or extraction may be performed before being supplied to the subsequent step (e.g., step E) (such post-treatment optionally being followed by isolation or purification). However, it is preferred that after post-treatment such as filtration, washing or extraction, the mixture is supplied to the subsequent step (e.g., step E) without isolation or purification.

In step D, there may be, for example, a case where a compound of general formula (VI'):

[Chemical Formula 24]

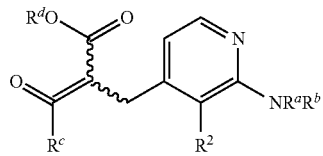
(VI')

[wherein $R^2$, $R^a$, $R^b$, $R^c$ and $R^d$ have the same definitions as above] (a keto-enol tautomer of the compound of general formula (VI)) is obtained in addition to the compound of general formula (VI). In that case, the compound of general formula (VI) may be supplied to the subsequent step without removal of the compound of general formula (VI').

In step D, the compound of general formula (VI) may be obtained via a compound of general formula (Va):

[Chemical Formula 25]

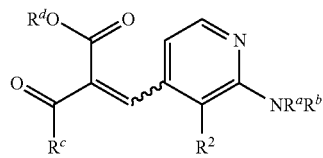
(Va)

[wherein $R^2$, $R^a$, $R^b$, $R^c$ and $R^d$ have the same definitions as above] and/or a compound of general formula (Vb):

[Chemical Formula 26]

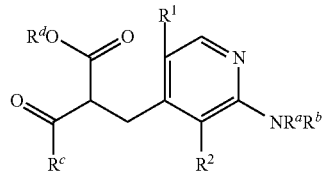
(Vb)

[wherein $R^1$, $R^2$, $R^a$, $R^b$, $R^c$ and $R^d$ have the same definitions as above].

The method of the present invention for producing a compound represented by general formula (VI) may consist of steps A to D.

The method of the present invention for producing a compound represented by general formula (VII) or a pharmaceutically acceptable salt thereof may further comprise steps E to G.

Step E:

Step E is a step in which the compound represented by general formula (VI) is reacted with a compound represented by general formula (VIII):

[Chemical Formula 27]

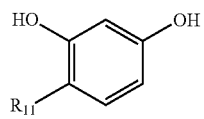
(VIII)

[wherein $R^{11}$ has the same definition as above] in the presence of an acid to obtain a compound represented by general formula (IX):

[Chemical Formula 28]

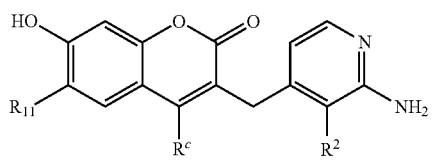
(IX)

[wherein $R^2$, $R^c$ and $R^{11}$ have the same definitions as above] or a pharmaceutically acceptable salt (acid salt) or acid adduct thereof.

Examples of the acid include inorganic acids (e.g., hydrochloric acid, hydrobromic acid, hydroiodic acid, sulfuric acid, and phosphoric acid), sulfonic acids (e.g., methanesulfonic acid, benzenesulfonic acid, and toluenesulfonic acid), and carboxylic acids (e.g., formic acid, acetic acid, oxalic acid, maleic acid, fumaric acid, citric acid, malic acid, succinic acid, malonic acid, gluconic acid, mandelic acid, benzoic acid, salicylic acid, fluoroacetic acid, trifluoroacetic acid, tartaric acid, propionic acid, and glutaric acid), with sulfonic acids being preferred and methanesulfonic acid being particularly preferred.

A solvent which is inert to the reaction can be used as a reaction solvent. Examples of such solvents include ether solvents (e.g., ether, tetrahydrofuran, dioxane, dimethoxyethane, and cyclopentyl methyl ether), aromatic hydrocarbon solvents (e.g., benzene, toluene, xylene, quinoline, and chlorobenzene), aliphatic hydrocarbon solvents (e.g., pentane, hexane, heptane, octane, and cyclohexane), amide solvents (e.g., N,N-dimethylformamide, N,N-dimethylacetamide, and N-methylpyrrolidone), alcohol solvents (e.g., methanol, ethanol, 2,2,2-trifluoroethanol, n-propanol, 2-propanol, n-butanol, sec-butanol, pentanol, hexanol, cyclopropanol, cyclobutanol, cyclopentanol, cyclohexanol, ethylene glycol, 1,3-propanediol, 1,4-butanediol, and 1,5-pentanediol), acetate ester solvents (e.g., methyl acetate, ethyl acetate, and isopropyl acetate), acetonitrile, and mixtures of (two or more of) them, with 2,2,2-trifluoroethanol being preferred. Acetate ester solvents are also preferred, with ethyl acetate being particularly preferred. When the mixture obtained upon completion of the reaction of step D is to be supplied to step E without post-treatment (e.g., filtration, washing, or extraction) and/or isolation or purification, the solvent used in step D (e.g., an acetate ester solvent such as ethyl acetate) may remain in the mixture, and step E can be performed without removal of the residual solvent.

The reaction temperature is generally −20° C. to 150° C., preferably −10° C. to 100° C. The reaction time may be appropriately determined depending on the reaction temperature and other factors, but it is generally 2 hours to 20 hours, preferably 2 hours to 10 hours.

If the acid is not neutralized after the reaction, a pharmaceutically acceptable salt or acid adduct of the compound of general formula (IX) is obtained. On the other hand, if a base (e.g., triethylamine, sodium carbonate, potassium carbonate, or sodium hydrogencarbonate) is added to neutralize the acid after the reaction, the free form of the compound of general formula (IX) is obtained.

When a pharmaceutically acceptable salt or acid adduct of the compound of general formula (IX) is obtained, a solvent can be added to the reaction mixture to precipitate the desired product as crystals. The solvent may be, for example, a combination of water and an alcohol solvent, preferably a combination of water and ethanol. When a combination of water and ethanol is to be used, this may be further combined with 2-propanol. A seed crystal can also be added to promote the crystal precipitation.

Step F:

Step F is a step in which the compound represented by general formula (IX) or the pharmaceutically acceptable salt or acid adduct thereof is reacted with X—Y [wherein X has the same definition as above and Y represents a halogen atom] in the presence of a base to obtain a compound represented by general formula (X):

[Chemical Formula 29]

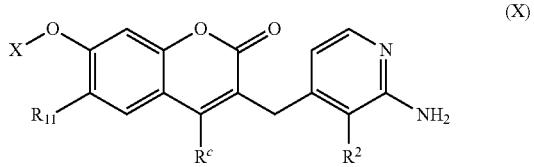

(X)

[wherein $R^2$, $R^c$, $R^{11}$ and X have the same definitions as above].

Examples of the base include weakly basic inorganic salts (e.g., sodium carbonate, potassium carbonate, and cesium carbonate) and metal hydrides (e.g., sodium hydride and potassium hydride), with potassium carbonate, cesium carbonate and sodium hydride being preferred.

Examples of reaction solvents which may be used include ether solvents (e.g., tetrahydrofuran and diethyl ether) and N,N-dimethylformamide, with tetrahydrofuran and N,N-dimethylformamide being preferred.

The reaction temperature may be appropriately determined depending on the reaction solvent and other factors. However, when X is an electron-deficient heteroaryl group (e.g., pyridyl or pyrimidinyl), it is generally 60° C. to 150° C., preferably 70° C. to 100° C. When X is an electron-rich heteroaryl group (e.g., thiazolyl), it is generally 90° C. to 200° C., preferably 100° C. to 120° C. When X is $R^3R^4NCO—$, it is generally 0° C. to 50° C., preferably 0° C. to 30° C. The reaction time may be appropriately determined depending on the reaction temperature and other factors, but it is generally 30 minutes to 5 hours, preferably 40 minutes to 2 hours.

When X is an electron-rich heteroaryl group (e.g., thiazolyl), the reaction may also be performed under microwave irradiation in the presence of a monovalent copper salt (e.g., copper(I) iodide, $CuPF_6$, or copper(I) trifluoromethanesulfonate), preferably copper(I) iodide, for example.

Step G:

Step G is a step in which the compound represented by general formula (X) is reacted with a compound represented by general formula (XI):

[Chemical Formula 30]

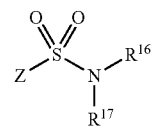

(XI)

[wherein $R^{16}$ and $R^{17}$ have the same definitions as above and Z represents a leaving group]
to obtain a compound represented by general formula (VII'):

[Chemical Formula 31]

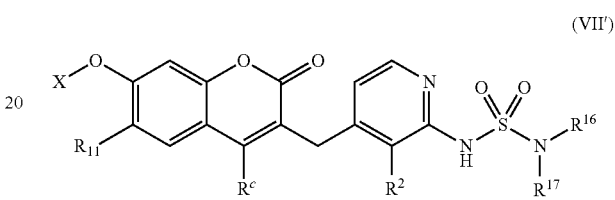

(VII')

[wherein $R^2$, $R^c$, $R^{11}$, X, $R^{16}$ and $R^{17}$ have the same definitions as above].

The leaving group represented by Z may be, for example, a halogen atom or a 2-oxazolidinon-3-yl group, with a halogen atom being preferred and a chlorine atom being particularly preferred.

Examples of reaction solvents which may be used include methylene chloride, acetonitrile, and N,N-dimethylformamide, with acetonitrile and N,N-dimethylformamide being preferred from the viewpoint of solubility of a compound of general formula (X).

The reaction may also be performed in the presence of a base. The base is preferably an organic amine (e.g., pyridine, triethylamine, or diisopropylethylamine).

The reaction temperature is generally 15° C. to 120° C., preferably 20° C. to 85° C. The reaction time is generally 1 hour to 2 days, preferably 2 hours to 24 hours.

A compound of general formula (VII) wherein $R^{15}$ is a $C_{1-6}$ alkyl group can be obtained by $C_{1-6}$ alkylation of a compound of general formula (VII'). The $C_{1-6}$ alkylation can be performed based on, for example, the method disclosed in Bioorganic Medicinal Chemistry 2005, 13, 1393-1402, Organic Preparations and Procedures International 2004, 36, 347-351, or Journal of Medicinal Chemistry 2004, 47, 6447-6450.

A pharmaceutically acceptable salt of a compound of general formula (VII) can be produced by contacting or reacting the compound with an acid or base that can be used in the production of pharmaceuticals. Examples of such salts include inorganic acid salts (e.g., hydrochloride, hydrobromide, hydroiodide, sulfate, and phosphate), sulfonates (e.g., methanesulfonate, benzenesulfonate, and toluenesulfonate), carboxylates (e.g., formate, acetate, oxalate, maleate, fumarate, citrate, malate, succinate, malonate, gluconate, mandelate, benzoate, salicylate, fluoroacetate, trifluoroacetate, tartarate, propionate, and glutarate), alkali metal salts (e.g., lithium salt, sodium salt, potassium salt, cesium salt, and rubidium salt), alkaline earth metal salts (e.g., magnesium salt and calcium salt), and ammonium salts (e.g., ammonium salt, alkylammonium salt, dialkylammonium salt, trialkylammonium salt, and tetraalkylammonium salt), with alkali metal salts being preferred and potassium salt being particularly preferred.

EXAMPLES

Preferred examples of the present invention will now be described in detail.

In the following examples, nuclear magnetic resonance (NMR) analysis was performed using a JEOL JNM-ECP500 nuclear magnetic resonance apparatus. Mass spectrometry (MS) was performed using a Waters LCT Premier XE mass spectrometer.

In the following descriptions, N,N-dimethylformamide is abbreviated as "DMF", tetrahydrofuran as "THF", high-performance liquid chromatography as "HPLC" and trifluoroacetic acid as "TFA". Also, "room temperature" means a temperature of 15° C. to 25° C.

Example 1

Step 1

Synthesis of 2-acetylamino-5-chloro-3-fluoropyridine

[Chemical Formula 32]

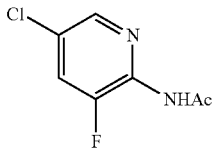

Under a nitrogen atmosphere, DMF (200 mL) and THF (830 mL) were added to acetamide (94.8 g, 1.61 mol), and the mixture was warmed to 50° C. A 40 wt % sodium hexamethyldisilazide THF solution (629 g, 1.37 mol) was added dropwise thereto, and the mixture was stirred for 2 hours at the same temperature. 5-Chloro-2,3-difluoropyridine (100.0 g, 0.67 mol) was then added, THF (20 mL) was further added, and the mixture was stirred for 3 hours at the same temperature. The reaction mixture was cooled to 0° C., 2.8 M HCl (500 mL) was added, the mixture was warmed to room temperature, and the organic layer was separated. The organic layer was washed with a 20 wt % sodium chloride aqueous solution (500 mL), and the solvent was distilled off under reduced pressure. THF (500 mL) was added to the residue, and the mixture was heated to 70° C. to dissolve the residue. After cooling to room temperature and confirming the precipitation of solids, n-heptane (1500 mL) was added, and the mixture was further cooled to 0° C. and stirred for 3 hours at that temperature. The precipitated crystals were collected by filtration, washed with a mixed solvent of THF (100 mL) and n-heptane (500 mL), and dried under reduced pressure to obtain the title compound (91.2 g).

Yield: 72%

$^1$H-NMR (CDCl$_3$) δ (ppm): 2.36 (3H, s), 7.49 (1H, dd, J=2.0, 9.5 Hz), 7.78 (1H, br), 8.17 (1H, d, J=2.0 Hz)

MS (ESI$^+$): 189 [M+1]$^+$

Step 2

Synthesis of 2-acetylamino-5-chloro-3-fluoro-4-formylpyridine

[Chemical Formula 33]

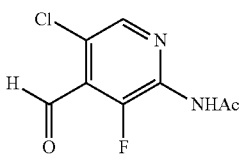

Under a nitrogen atmosphere, 2-acetylamino-5-chloro-3-fluoropyridine (70.0 g, 0.37 mol) and 4-formylmorpholine (128.2 g, 1.11 mol) were dissolved in THF (840 mL) at room temperature. The solution was cooled to −20° C., a 24 wt % lithium hexamethyldisilazide THF solution (595 g, 0.85 mol) was added dropwise, and the mixture was stirred for 5.5 hours at that temperature. The reaction mixture was added to an aqueous solution of citric acid monohydrate (257 g) and sodium chloride (70 g) in water (420 mL) while stirring at 0° C. The organic layer was separated, and washed with a 50 wt % dipotassium hydrogenphosphate aqueous solution (350 mL) and a 20 wt % sodium chloride aqueous solution (350 mL) in that order to obtain an organic layer (1458 g). A portion (292 g) of the organic layer was sampled for analysis, and the solvent was distilled off from the remainder (1166 g) under reduced pressure. THF (350 mL) was added to the residue, and the solvent was distilled off under reduced pressure. THF (350 mL) was again added to the residue, and the solvent was distilled off under reduced pressure to obtain a solid (81.4 g) containing the title compound. The product was used in the subsequent step without further purification.

The solvent was distilled off from a portion (29 g) of the sampled organic layer (292 g) under reduced pressure. The residue was subjected to silica gel column chromatography [eluent: AcOEt/hexane (1/4 to 9/1)] to obtain the title compound (1.05 g, 4.85 mmol) as a white powdery solid.

Yield: 66%

$^1$H-NMR (CDCl$_3$) δ (ppm): 2.40 (3H, s), 7.59 (1H, br), 8.34 (1H, br), 10.42 (1H, s)

MS (ESI$^+$): 217 (M+1)

Step 3

Synthesis of 2-[(2-acetylamino-3-fluoropyridin-4-yl)methyl]-3-oxobutanoic acid ethyl ester

[Chemical Formula 34]

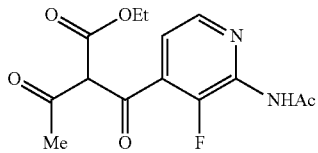

Under a nitrogen atmosphere, the solid product of step 2 (81.4 g) was dissolved in 2,2,2-trifluoroethanol (448 mL), piperidine (4.4 g, 51.7 mmol), acetic acid (3.1 g, 51.7 mmol) and ethyl 3-oxobutanoate (37.0 g, 0.28 mol) were added, and after warming to 50° C., the mixture was stirred for 3 hours.

After cooling the reaction mixture to room temperature, a solution of triethylamine (758 mL, 5.5 mol) and formic acid (172 mL, 4.6 mol) in 2-propanol (1248 mL) and 20% Pd(OH)$_2$ carbon (21.2 g; water content: 46.2%) were added, and after warming to 50° C., the mixture was stirred for 4 hours. The reaction mixture was filtered through celite, and the residue was washed with 2-propanol (679 mL) The filtrate and wash solution were combined (2795 g), and the solvent was distilled off from a portion (399 g) thereof under reduced pressure (preserving the remainder (2396 g)). Ethyl acetate (24.2 mL) was added to the residue obtained by distilling off the solvent, and the solvent was distilled off under reduced pressure. Ethyl acetate (182 mL) was again added to the residue, the organic layer was washed with a 20 wt % sodium chloride aqueous solution (61 mL), a 10 wt % potassium dihydrogenphosphate aqueous solution (61 mL) and a 20 wt % sodium chloride aqueous solution (61 mL) in that order, and the solvent was distilled off under reduced pressure. 2,2,2-Trifluoroethanol (24 mL) was then added to the residue, and the solvent was distilled off under reduced pressure to obtain an oily product (15.0 g) containing the title compound. The product was used in the subsequent step without further purification.

$^1$H-NMR (CDCl$_3$) δ (ppm): 1.24 (3H, t, J=7.0 Hz), 2.27 (3H, s), 2.37 (3H, s), 3.16-3.26 (2H, m), 3.86 (1H, t, J=7.5 Hz), 4.15-4.22 (2H, m), 6.98 (1H, t, J=5.0 Hz), 7.68 (1H, br), 8.05 (1H, d, J=5.0 Hz)

MS (ESI$^+$): 297 (M+1)

Step 4

Synthesis of 3-(3-fluoro-2-aminopyridin-4-ylmethyl)-7-hydroxy-4-methyl-2-oxo-2H-1-benzopyran methanesulfonate

[Chemical Formula 35]

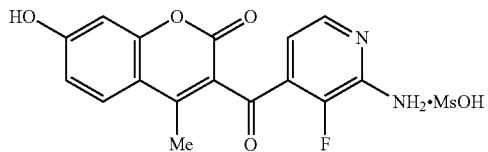

Under a nitrogen atmosphere, the oily product of step 3 (15.0 g) was dissolved in 2,2,2-trifluoroethanol (33 mL) Resorcinol (5.3 g, 47.9 mmol) and methanesulfonic acid (11.7 mL, 181 mmol) were added thereto at 24° C., and the mixture was stirred at 90° C. for 4 hours. The mixture was cooled to room temperature and allowed to stand for 13 hours, ethanol (33 mL) and water (11 mL) were then added, and the mixture was stirred at 90° C. for 4.5 hours. It was cooled to 55° C., 2-propanol (105 mL) was added, and the mixture was cooled to room temperature and allowed to stand for 14 hours. The precipitated crystals were collected by filtration, washed twice with 2-propanol (33 mL), and dried under reduced pressure to obtain the title compound (8.2 g).

Yield (overall yield from the 2-acetylamino-5-chloro-3-fluoropyridine used in step 2): 49%

MS (ESI$^+$): 301 [M+1−MsOH]$^+$

Step 5

Synthesis of 4-methyl-3-(3-fluoro-2-aminopyridin-4-ylmethyl)-7-(pyrimidin-2-yloxy)-2-oxo-2H-1-benzopyran

[Chemical Formula 36]

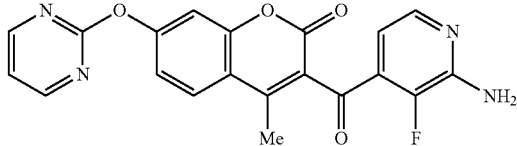

Under a nitrogen atmosphere, 3-(3-fluoro-2-aminopyridin-4-ylmethyl)-7-hydroxy-4-methyl-2-oxo-2H-1-benzopyran methanesulfonate (7.6 g, 19.2 mmol) and 2-bromopyrimidine (4.0 g, 24.9 mmol) were dissolved in DMF (122 mL), potassium carbonate (5.8 g, 42.2 mmol) was added, and the mixture was stirred at 115° C. for 3.5 hours. The reaction mixture was cooled to 28° C., water (122 mL) was added dropwise over a period of 0.5 hours at that temperature, and the mixture was stirred for 2 minutes. The mixture was further cooled to 0° C. and stirred for 1 hour, and the precipitated crystals were collected by filtration. The obtained crystals were washed with water (61 mL) and acetonitrile (61 mL) in that order, and dried under reduced pressure to obtain the title compound as crystals (6.5 g).

A portion (0.1 g) of the crystals was sampled for analysis, and the remainder (6.4 g) was suspended in DMF (70 mL) The suspension was heated to 60° C. and stirred for 5 minutes, acetonitrile (185 mL) was then added at that temperature, and the mixture was stirred for 80 minutes. It was then cooled to 40° C. and stirred for 0.5 hours, and further cooled to 25° C. and stirred for 0.5 hours. The mixture was further cooled to 0° C. and stirred for 1.5 hours, and the precipitated crystals were collected by filtration. The obtained crystals were washed with acetonitrile (46 mL), and dried under reduced pressure to obtain the title compound (5.5 g). The title compound is a compound disclosed in WO 2007/091736.

Yield: 76%

Step 6

Synthesis of 3-{2-(methylaminosulfonyl)amino-3-fluoropyridin-4-ylmethyl}-4-methyl-7-(pyridin-2-yloxy)-2-oxo-2H-1-benzopyran

[Chemical Formula 37]

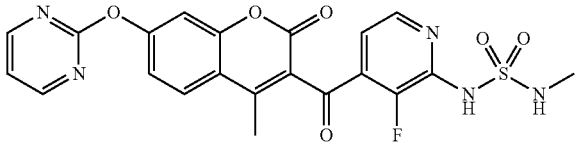

Under a nitrogen atmosphere, the compound 4-methyl-3-(3-fluoro-2-aminopyridin-4-ylmethyl)-7-(pyrimidin-2-yloxy-2-oxo-2H-1-benzopyran (1.7 g, 4.5 mmol) was suspended in DMF (18 mL) Pyridine (0.8 mL, 9.9 mmol) was added thereto, the mixture was cooled to 10° C., and a solution of N-methylsulfamoyl chloride (1.05 g, 8.1 mmol) in acetonitrile (18 mL) was added dropwise while maintaining an internal temperature of 15° C. or lower. The mixture was stirred at the same temperature for 90 minutes, acetonitrile (3.4 mL) was then added, and water (50 mL) was further added dropwise while maintaining an internal temperature of 20° C. or lower. The external temperature was lowered to 0° C., and after the internal temperature reached 5° C., the mixture was stirred for 2 hours. The precipitated crystals were collected by filtration, washed with water (8.5 mL), and dried to obtain the title compound (1.9 g, 4.0 mmol).

Yield: 88%

MS (ESI+): 472 [M+1]+

Step 7

Synthesis of 3-{2-(methylaminosulfonyl)amino-3-fluoropyridin-4-ylmethyl}-4-methyl-7-(pyridin-2-yloxy)-2-oxo-2H-1-benzopyran potassium salt

[Chemical Formula 38]

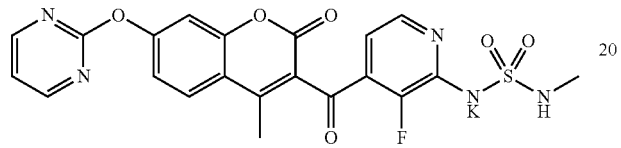

Under a nitrogen atmosphere, the compound 3-{2-(methylaminosulfonyl)amino-3-fluoropyridin-4-ylmethyl}-4-methyl-7-(pyridin-2-yloxy)-2-oxo-2H-1-benzopyran (1.6 g, 3.4 mmol) was suspended in THF (10 mL), and water (3 mL) was added. A 2.0 M potassium hydroxide aqueous solution (1.8 mL, 3.6 mmol) was added dropwise thereto at 25° C. over a period of 10 minutes, and after warming to 60° C., the mixture was stirred at that temperature for 2 hours. The reaction mixture was cooled to 20° C., and THF (8 mL) was added dropwise over a period of 30 minutes. The external temperature was lowered to −5° C., and after the internal temperature reached 0° C., the mixture was stirred for 160 minutes. The precipitated crystals were collected by filtration, and washed with a mixture of THF (14 mL) and water (1.6 mL) (precooled to 5° C.). They were further washed with THF (8 mL), and dried to obtain the title compound (0.72 g, 1.4 mmol).

Yield: 42%

MS (ESI+): 472 [M+2H−K]+

Example 2

Synthesis of 2-[(2-acetylamino-5-chloro-3-fluoropyridine)methylene]-3-oxobutanoic acid ethyl ester

[Chemical Formula 39]

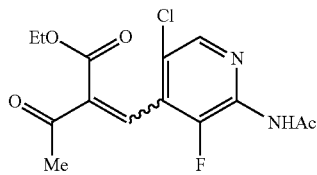

A solid product (containing 2-acetylamino-5-chloro-3-fluoro-4-formylpyridine) (327 mg) obtained in the same manner as steps 1 and 2 of Example 1 was dissolved in 2,2,2-trifluoroethanol (1.6 mL), piperidine (18 µL, 0.18 mmol), acetic acid (11 µL, 0.18 mmol) and ethyl 3-oxobutanoate (134 µL, 1.1 mmol) were added, and after warming to 50° C., the mixture was stirred for 3 hours. After cooling to room temperature, ice-cold water was added to the reaction mixture, and extraction was performed with ethyl acetate. The organic layer was washed with brine and dried over anhydrous sodium sulfate, and the solvent was distilled off under reduced pressure to obtain a crude product. The product was purified by column chromatography [eluent: n-heptane/ethyl acetate (1/1 to 1/4)] to obtain the title compound (mixture of E and Z isomers) (277 mg).

Yield: 92%

1H-NMR (CDCl3) (mixture of E and Z isomers) δ (ppm): 1.13 (1.7H, t, J=7.0 Hz), 1.37 (1.3H, t, J=7.0 Hz), 2.32 (1.3H, s), 2.33 (1.7H, s), 2.43 (1.3H, d, J=1.5 Hz), 2.49 (1.7H, s), 4.22 (1.1H, q, J=7.0 Hz), 4.36 (0.9H, q, J=7.0 Hz), 7.42-7.43 (1H, m), 8.01 (0.4H, brs), 8.04 (0.6H, brs), 8.20 (0.4H, s), 8.22 (0.6H, s)

MS (ESL): 329 (M+1)

Example 3

Synthesis of 2-[(2-acetylamino-5-chloro-3-fluoropyridin-4-yl)methyl]-3-oxobutanoic acid ethyl ester

[Chemical Formula 40]

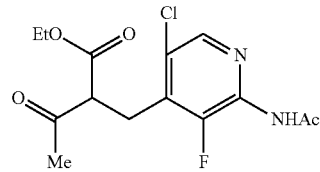

The compound 2-[(2-acetylamino-5-chloro-3-fluoropyridine)methylene]-3-oxobutanoic acid ethyl ester (50 mg) was dissolved in a mixed solvent of 2-propanol (0.8 mL) and ethyl acetate (0.8 mL) 10% Pd(OH)2 carbon (PE-Type, N.E. CHEMCAT) (7 mg; water content: 51.8%) was added thereto, and the mixture was stirred for 40 minutes at room temperature under a hydrogen atmosphere. The reaction mixture was filtered, and the solvent was distilled off under reduced pressure to obtain a crude product. The product was purified by column chromatography [eluent: n-heptane/ethyl acetate (1/1 to 1/2)] to obtain the title compound (39 mg) as a solid.

Yield: 78%

1H-NMR (CDCl3) δ (ppm): 1.23 (3H, t, J=7.0 Hz), 2.27 (3H, s), 2.35 (3H, s), 3.29-3.39 (2H, m), 3.89 (1H, t, J=7.5 Hz), 4.18 (2H, q, 7.0 Hz), 7.69 (1H, br), 8.16 (1H, s)

MS (ESI+): 353 (M+Na)

Example 4

Synthesis of 3-(3-fluoro-2-acetylaminopyridin-4-ylmethyl)-7-hydroxy-4-methyl-2-oxo-2H-1-benzopyran and 3-(3-fluoro-2-aminopyridin-4-ylmethyl)-7-hydroxy-4-methyl-2-oxo-2H-1-benzopyran

[Chemical Formula 41]

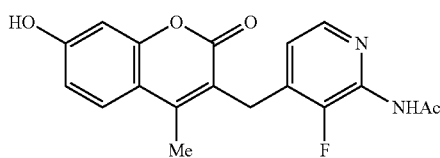

-continued

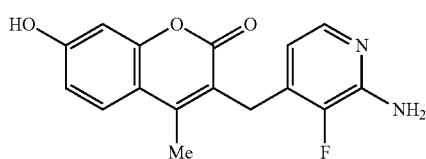
[Chemical Formula 42]

Under a nitrogen atmosphere, the compound 2-[(2-acetylamino-3-fluoropyridin-4-yl)methyl]-3-oxobutanoic acid ethyl ester (122 mg, 0.41 mmol) was dissolved in 2,2,2-trifluoroethanol (360 μL). Resorcinol (59 mg, 0.53 mmol) and methanesulfonic acid (130 μL, 2.0 mmol) were added thereto at room temperature, and the mixture was stirred at 85° C. for 3 hours. The mixture was cooled to 0° C., triethylamine was added, and after the mixture was warmed to room temperature, the solvent was distilled off under reduced pressure to obtain a crude product. The product was purified by column chromatography [eluent: dichloromethane/methanol (20/1 to 10/1)] to obtain the title compounds [3-(3-fluoro-2-acetylaminopyridin-4-ylmethyl)-7-hydroxy-4-methyl-2-oxo-2H-1-benzopyran (64 mg) and 3-(3-fluoro-2-aminopyridin-4-ylmethyl)-7-hydroxy-4-methyl-2-oxo-2H-1-benzopyran (31 mg)] each as solids.

3-(3-Fluoro-2-acetylaminopyridin-4-ylmethyl)-7-hydroxy-4-methyl-2-oxo-2H-1-benzopyran Yield: 46%
MS (ESI+): 365 [M+Na]+

3-(3-Fluoro-2-aminopyridin-4-ylmethyl)-7-hydroxy-4-methyl-2-oxo-2H-1-benzopyran

Yield: 25%
MS (EST): 323 [M+Na]+

Example 5

Step 1

Synthesis of 2-acetylamino-5-chloro-3-fluoropyridine

[Chemical Formula 43]

Under a nitrogen atmosphere, DMF (14 mL) and THF (44 mL) were added to acetamide (6.6 g, 112 mmol), and the mixture was warmed to 50° C. A 1.9 M sodium hexamethyldisilazide THF solution (51 mL, 96 mmol) was added dropwise thereto, and the mixture was stirred for 3 hours at the same temperature. 5-Chloro-2,3-difluoropyridine (7.0 g) was then added, THF (1.4 mL) was further added, and the mixture was stirred for 3 hours at the same temperature. The reaction mixture was cooled to 0° C., an aqueous solution of citric acid monohydrate (20 g) and sodium chloride (4.9 g) in water (35 mL) was added, the mixture was warmed to room temperature, and the organic layer was separated. The organic layer was washed with a 20 wt % sodium chloride aqueous solution (35 mL), and the solvent was distilled off under reduced pressure. A mixed solvent (70 mL) of heptane and tert-butyl methyl ether (15:1) and water (35 mL) were added to the residue, and the mixture was stirred for 10 minutes at room temperature. The mixture was filtered, and the obtained solid was washed twice with water (35 mL). It was further washed with a mixed solvent (70 mL) of heptane and tert-butyl methyl ether (15:1), and dried under reduced pressure to obtain the title compound (6.5 g).

Yield: 74%
The 1H-NMR and MS spectra matched those of the title compound obtained in Example 1 (step 1).

Step 2

Synthesis of 2-acetylamino-5-chloro-3-fluoro-4-formylpyridine

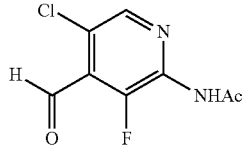
[Chemical Formula 44]

Under a nitrogen atmosphere, 2-acetylamino-5-chloro-3-fluoropyridine (6.0 g) and DMF (7.4 mL, 95 mmol) were dissolved in THF (60 mL). The solution was cooled to −20° C., a 1.0 M lithium hexamethyldisilazide THF solution (127 mL, 127 mmol) was added dropwise, and the mixture was stirred for 5 hours at that temperature. The reaction mixture was added to an aqueous solution of citric acid monohydrate (33 g) and sodium chloride (7.5 g) in water (48 mL) while stirring at 0° C., the mixture was warmed to room temperature, and the organic layer was separated. The organic layer was washed with a 40 wt % dipotassium hydrogenphosphate aqueous solution (30 mL) and a 20 wt % sodium chloride aqueous solution (30 mL) in that order, and the solvent was distilled off under reduced pressure. THF (30 mL) was added to the residue, and the solvent was distilled off under reduced pressure. THF (30 mL) was again added to the residue, and the solvent was distilled off under reduced pressure to obtain a solid (7.3 g) containing the title compound. The product was used in the subsequent step without further purification.

The 1H-NMR and MS spectra matched those of the title compound obtained in Example 1 (step 2).

Steps 3 and 4

Synthesis of 3-(3-fluoro-2-aminopyridin-4-ylmethyl)-7-hydroxy-4-methyl-2-oxo-2H-1-benzopyran methanesulfonate

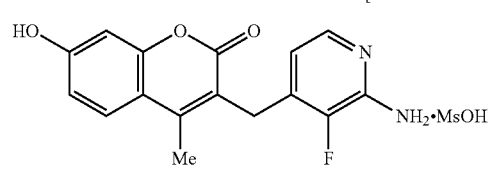
[Chemical Formula 45]

Under a nitrogen atmosphere, acetonitrile (45 mL), piperidine (0.5 mL, 5.2 mmol), acetic acid (0.3 mL, 5.2 mmol) and ethyl 3-oxobutanoate (3.6 mL, 29 mmol) were added to the solid product of step 2 (7.3 g) at room temperature, and after warming to 50° C., the mixture was stirred for 4.5 hours. After cooling the reaction mixture (47 g) to room temperature, a portion (5 g) thereof was removed. 2-Propanol (36 mL), a solution of triethylamine (69 mL, 496 mmol) and formic acid (16 mL, 409 mmol) in 2-propanol (78 mL), and 20% Pd(OH)$_2$ carbon (3.9 g; water content: 50%) were added to the remaining reaction mixture (42 g), and after warming to 50° C., the mixture was stirred for 5.5 hours. After cooling to room temperature, the reaction mixture was filtered through celite, and the residue was washed with ethyl acetate (386 mL). The filtrate and wash solution were combined, and washed twice with a 10 wt % sodium chloride aqueous solution (116 mL). The organic layer was washed with a saturated sodium bicarbonate solution (116 mL) and a 20 wt % sodium chloride aqueous solution (116 mL) in that order, and the solvent was distilled off under reduced pressure. Ethyl acetate (77 mL) was added to the residue obtained by distilling off the solvent, and the mixture was washed with water (39 mL) and a 20 wt % sodium chloride aqueous solution (39 mL) in that order to obtain an organic layer (124.2 g). After removing a portion (0.36 g) of the organic layer, the solvent was distilled off from the remainder (123.8 g) under reduced pressure to obtain an oily product (7.0 g) containing the title compound.

The oily product was dissolved in 2,2,2-trifluoroethanol (15 mL), resorcinol (2.4 g, 21 mmol) and methanesulfonic acid (5.3 mL, 81 mmol) were added at room temperature, and the mixture was stirred at 95° C. for 16 hours. After cooling the reaction mixture to room temperature, ethanol (15 mL) and water (4.9 mL) were added, and the mixture was stirred at 95° C. for 3 hours. The solution was cooled to 55° C., 2-propanol (47 mL) was added, and after cooling to room temperature, the mixture was stirred for 1.5 hours. The precipitated crystals were collected by filtration, washed twice with 2-propanol (15 mL), and dried under reduced pressure to obtain a solid (4.0 g) containing the title compound. The product was used in the subsequent step without further purification.

The content of the title compound in the solid was determined by $^1$H-NMR analysis (internal standard: N,N-dimethylacetamide), and the yield of the title compound was calculated on that basis.

Content: 79%

Yield (overall yield from the 2-acetylamino-5-chloro-3-fluoropyridine used in step 2): 28%

The MS spectrum matched that of the title compound obtained in Example 1 (step 4).

Step 5

Synthesis of 4-methyl-3-(3-fluoro-2-aminopyridin-4-ylmethyl)-7-(pyrimidin-2-yloxy)-2-oxo-2H-1-benzopyran

[Chemical Formula 46]

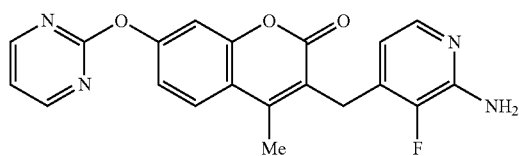

Under a nitrogen atmosphere, potassium carbonate (2.3 g, 17 mmol) was added to a solution of the solid product of step 4 (3.0 g) and 2-bromopyrimidine (1.6 g, 9.8 mmol) in DMF (48 mL), and the mixture was stirred at 115° C. for 2.5 hours. The reaction mixture was cooled to 28° C., water (48 mL) was added dropwise over a period of 5 minutes at that temperature, and after cooling to 0° C., the mixture was stirred for 2 hours. The precipitated crystals were collected by filtration, washed with water (24 mL) and acetonitrile (24 mL) in that order, and dried under reduced pressure to obtain crude crystals (2.3 g). DMF (65 mL) was added to the crude crystals (2.3 g), and after heating to 60° C. and confirming the dissolution, the mixture was cooled to 25° C. Water (65 mL) was added at 25° C., and the mixture was further cooled to 0° C. and stirred for 4 hours. The precipitated crystals were collected by filtration, washed with water (22 mL) and acetonitrile (22 mL) in that order, and dried under reduced pressure to obtain the title compound (2.1 g). The title compound is a compound disclosed in WO 2007/091736.

Yield (overall yield from the 2-acetylamino-5-chloro-3-fluoropyridine used in step 2): 27%

Example 6

Synthesis of 2-acetylamino-5-chloro-3-fluoropyridine

[Chemical Formula 47]

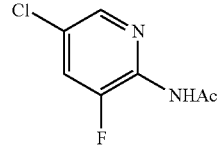

Under a nitrogen atmosphere, a suspension of acetamide (620 mg, 10.5 mmol) and potassium t-butoxide (1.01 g, 10.5 mmol) in DMF (4.5 mL) was heated to 50° C. and stirred for 1.5 hours. It was cooled to 0° C., 5-chloro-2,3-difluoropyridine (450 mg, 3.0 mmol) was added dropwise, DMF (0.45 mL) was further added, and the mixture was stirred at that temperature for 2.5 hours. A saturated ammonium chloride aqueous solution (4.5 mL) and water (4.5 mL) were added to the reaction mixture in that order, and extraction was performed with ethyl acetate (9.0 mL). The aqueous layer was extracted twice with ethyl acetate (9.0 mL), and the combined organic layers were washed with a sodium chloride aqueous solution (4.5 mL) and dried over anhydrous sodium sulfate. A portion (22.1%) of the organic layer was sampled for $^1$H-NMR quantification, and the solvent was distilled off from the remaining organic layer under reduced pressure. A mixed solvent (7.0 mL) of heptane and t-butyl methyl ether (15:1) was added to the residue to form a suspension, and the suspension was stirred. The precipitated solid was collected by filtration, washed with a mixed solvent (3.5 mL) of heptane and t-butyl methyl ether (15:1), and dried under reduced pressure to obtain the title compound (321 mg, 1.7 mmol).

The yield was calculated by $^1$H-NMR analysis (internal standard: 1,2,4,5-tetramethylbenzene) of the previously sampled organic layer.

Yield: 78%

$^1$H-NMR (CDCl$_3$) δ (ppm): 2.37 (3H, s), 7.49 (1H, dd, J=2.0, 9.5 Hz), 7.62 (1H, br), 8.18 (1H, d, J=2.0 Hz)

MS (ESI$^+$): 189 [M+1]$^+$

Example 7

Synthesis of 2-acetylamino-5-chloro-3-fluoropyridine

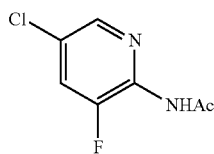

[Chemical Formula 48]

Under a nitrogen atmosphere, acetamide (4.1 g, 70 mmol) was dissolved in DMF (30 mL). Sodium hydride (content: 50% to 72%, 2.4 g, 60 mmol (the content being regarded as 60%)) was added thereto at 0° C. in three portions. The compound 5-chloro-2,3-difluoropyridine (3.0 g, 20 mmol) was then added dropwise at 0° C., and the mixture was stirred for 3 hours, during which time the temperature was allowed to increase to room temperature. The reaction mixture was cooled to 0° C., a saturated ammonium chloride aqueous solution was added, and after the mixture was warmed to room temperature, extraction was performed with ethyl acetate. The organic layer was washed with brine and dried over anhydrous sodium sulfate, and the solvent was distilled off under reduced pressure. The residue was suspended in a mixed solvent of heptane and t-butyl methyl ether (15:1), and the suspension was stirred at room temperature. The suspension was filtered, and the obtained solid was dried under reduced pressure to obtain the title compound (2.7 g).

Yield: 70%

The $^1$H-NMR and MS spectra matched those of the title compound obtained in Example 1 (step 1).

Example 8

Synthesis of 2-acetylamino-5-chloro-3-fluoro-4-formylpyridine

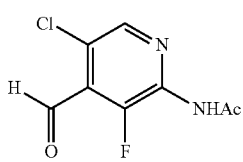

[Chemical Formula 49]

Under a nitrogen atmosphere, 2-acetylamino-5-chloro-3-fluoropyridine (20 mg, 0.11 mmol) and 4-formylmorpholine (64 μL, 0.64 mmol) were dissolved in THF (0.2 mL) at room temperature. The solution was cooled to −20° C., a 1.0 M lithium hexamethyldisilazide THF solution (244 μL, 0.24 mmol) was added dropwise, and the mixture was stirred for 2 hours at that temperature. The reaction mixture was subjected to HPLC analysis under the following conditions, and the purity and conversion rate were calculated from the area ratio of the title compound and the starting compound (2-acetylamino-5-chloro-3-fluoropyridine). The formula used was: Conversion rate (%)=100−(area ratio of starting compound).

Purity: 96.8%

Conversion rate: 97.6%

HPLC conditions:

Column: TOSOH TSK-GEL ODS-100V (4.6 mm I.D.×7.5 cm, 3 μm)

Mobile phase: Solution A: H$_2$O/TFA (2000/1); Solution B: acetonitrile/TFA (2000/1)

Gradient operation: Solution B: 0% (3 minutes), 0% to 30% (10 minutes), 30% (3 minutes), 30% to 100% (6 minutes), 100% (1 minute)

Flow rate: 1.0 mL/min

Temperature: 30.0° C.

Detection wavelength: 287 nm

Example 9

Synthesis of 2-acetylamino-5-chloro-3-fluoro-4-formylpyridine

[Chemical Formula 50]

Under a nitrogen atmosphere, 2-acetylamino-5-chloro-3-fluoropyridine (50 mg, 0.27 mmol) and DMF (123 μL, 1.6 mmol) were dissolved in THF (0.5 mL) at room temperature. The solution was cooled to −20° C., a 24 wt % lithium hexamethyldisilazide THF solution (492 μL, 0.61 mmol) was added dropwise, and the mixture was stirred for 3 hours at that temperature. The reaction mixture was subjected to HPLC analysis under the same conditions as Example 8, and the purity and conversion rate were calculated from the area ratio of the title compound and the starting compound (2-acetylamino-5-chloro-3-fluoropyridine). The formula used was: Conversion rate (%)=100−(area ratio of starting compound).

Purity: 76.3%

Conversion rate: 77.1%

Example 10

Synthesis of 2-[(2-acetylamino-3-fluoropyridin-4-yl)methyl]-3-oxobutanoic acid ethyl ester

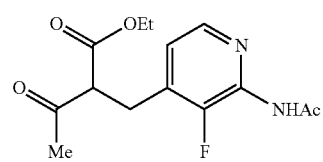

[Chemical Formula 51]

Under a nitrogen atmosphere, acetonitrile (0.4 mL), piperidine (5 μL, 0.046 mmol), acetic acid (3 μL, 0.046 mmol) and ethyl 3-oxobutanoate (34 μL, 0.27 mmol) were added to a solid product (containing 2-acetylamino-5-chloro-3-fluoro-4-formylpyridine) (114 mg) obtained in the same manner as steps 1 and 2 of Example 1, and after warming to 50° C., the mixture was stirred for 6 hours. The reaction mixture was subjected to HPLC analysis under the following conditions, and the purity and conversion rate were calculated from the area ratio of the product (2-[(2-acetylamino-5-chloro-3-fluoropyridine)methylene]-3-oxobutanoic acid ethyl ester) and the starting compound (2-acetylamino-5-chloro-3-fluoro-4-formylpyridine). The formula used was: Conversion rate (%)=100−(area ratio of starting compound).

Purity: 86.3%
Conversion rate: 99.3%
HPLC conditions (1):
Column: TOSOH TSK-GEL ODS-100V (4.6 mm I.D.×7.5 cm, 3 μm)
Mobile phase: Solution A: $H_2O$/TFA (2000/1); Solution B: acetonitrile/TFA (2000/1)
Gradient operation: Solution B: 0% (3 minutes), 0% to 30% (10 minutes), 30% (3 minutes), 30% to 100% (6 minutes), 100% (1 minute)
Flow rate: 1.0 mL/min
Temperature: 30.0° C.
Detection wavelength: 210 nm After cooling the reaction mixture to room temperature, a solution of triethylamine (670 μL, 4.9 mmol) and formic acid (150 μL, 4.0 mmol) in 2-propanol (1.1 mL) and 20% $Pd(OH)_2$ carbon (19 mg; water content: 50%) were added, and after warming to 50° C., the mixture was stirred for 4.5 hours. The reaction mixture was subjected to HPLC analysis under the following conditions, and the purities of the title compound and its precursor (2-[(2-acetylamino-5-chloro-3-fluoropyridin-4-yl)methyl]-3-oxobutanoi c acid ethyl ester) were calculated from their respective area ratios.

Purity: Title compound: 82.2%; Precursor: 7.3%
HPLC conditions (2):
Column: TOSOH TSK-GEL ODS-100V (4.6 mm I.D.×7.5 cm, 3 μm)
Mobile phase: Solution A: $H_2O$/TFA (2000/1); Solution B: acetonitrile/TFA (2000/1)
Gradient operation: Solution B: 0% (3 minutes), 0% to 30% (10 minutes), 30% (3 minutes), 30% to 100% (6 minutes), 100% (1 minute)
Flow rate: 1.0 mL/min
Temperature: 30.0° C.
Detection wavelength: 210 nm Example 11

Synthesis of 2-[(2-acetylamino-3-fluoropyridin-4-yl)methyl]-3-oxobutanoic acid ethyl ester

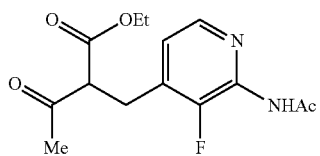

[Chemical Formula 52]

Under a nitrogen atmosphere, 2,2,2-trifluoroethanol (0.4 mL), piperidine (5 μL, 0.046 mmol), acetic acid (3 μL, 0.046 mmol) and ethyl 3-oxobutanoate (34 μL, 0.27 mmol) were added to a solid product (containing 2-acetylamino-5-chloro-3-fluoro-4-formylpyridine) (114 mg) obtained in the same manner as steps 1 and 2 of Example 1, and after warming to 50° C., the mixture was stirred for 5 hours. The reaction mixture was subjected to HPLC analysis under the same conditions as HPLC conditions (1) of Example 10, and the purity and conversion rate were calculated from the area ratio of the product (2-[(2-acetylamino-5-chloro-3-fluoropyridine)methylene]-3-oxobutanoi c acid ethyl ester) and the starting compound (2-acetylamino-5-chloro-3-fluoro-4-formylpyridine). The formula used was: Conversion rate (%)=100−(area ratio of starting compound).

Purity: 89.9%
Conversion rate: 99.5%

After cooling the reaction mixture to room temperature, a solution of triethylamine (670 μL, 4.9 mmol) and formic acid (150 μL, 4.0 mmol) in 2-propanol (1.1 mL) and 20% $Pd(OH)_2$ carbon (19 mg; water content: 50%) were added, and after warming to 50° C., the mixture was stirred for 4.5 hours. The reaction mixture was subjected to HPLC analysis under the same conditions as HPLC conditions (2) of Example 10, and the purities of the title compound and its precursor (2-[(2-acetylamino-5-chloro-3-fluoropyridin-4-yl)methyl]-3-oxobutanoic acid ethyl ester) were calculated from their respective area ratios.

Purity: Title compound: 89.3%; Precursor: 0.4%

Example 12

Reduction of 2-[(2-acetylamino-5-chloro-3-fluoropyridine)methylene]-3-oxobutanoic acid ethyl ester by hydrogenation

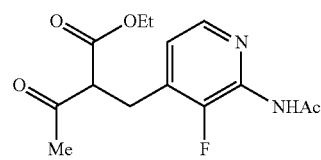

[Chemical Formula 53]

The compound 2-[(2-acetylamino-5-chloro-3-fluoropyridine)methylene]-3-oxobutanoic acid ethyl ester (13 mg) obtained in the same manner as Example 2 was dissolved in a mixed solvent of methanol (0.2 mL) and ethyl acetate (0.02 mL) 10% $Pd(OH)_2$ carbon (PE-Type, N.E. CHEMCAT) (2 mg; water content: 51.8%) was added thereto, and the mixture was stirred for 1.5 hours at room temperature under a hydrogen atmosphere. The reaction mixture was filtered, and the solvent was distilled off under reduced pressure to obtain a crude product. The product was purified by column chromatography [elution with n-heptane/ethyl acetate (1/1 to 0/1), followed by elution with ethyl acetate/methanol (15/1)] to obtain an oily product (1 mg).

Yield: 9%

The $^1$H-NMR and MS spectra matched those of the compound obtained in Example 1 (step 3).

Example 13

Steps 1 and 2

Synthesis of 2-acetylamino-5-chloro-3-fluoro-4-formylpyridine

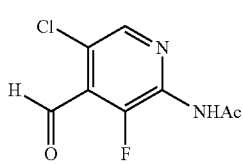

[Chemical Formula 54]

A solid (3.43 g) containing the title compound was obtained in the same manner as steps 1 and 2 of Example 1. The product was used in the subsequent step without further purification.

Step 3

Synthesis of 2-[(2-acetylamino-3-fluoropyridin-4-yl)methyl]-3-oxobutanoic acid ethyl ester

[Chemical Formula 55]

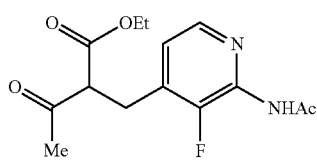

Under a nitrogen atmosphere, water (8.0 mL) was added to the solid product of step 2 (3.43 g), 3-oxobutanoic acid (1.32 g, 10.1 mmol), ethylenediamine diacetate (830 mg, 4.61 mmol), toluene (10.0 mL) and ethyl acetate (6.0 mL) were further added while stirring, and after warming to 40° C., the mixture was stirred for 5 hours. The reaction mixture was cooled to room temperature, the organic layer was separated, and 2-propanol (12.1 mL) was added to the organic layer. 20% Pd(OH)$_2$ carbon (1.52 g; water content: 46.2%) and a solution of triethylamine (20.3 g, 201 mmol) and formic acid (7.43 g, 161 mmol) in 2-propanol (10.6 mL) were further added in that order while stirring, and after warming to 50° C., the mixture was stirred for 3 hours. The reaction mixture was filtered through celite, and the residue was washed with 2-propanol (30.3 mL). The filtrate and wash solution were combined, the solvent was distilled off under reduced pressure, ethyl acetate (6.1 mL) was added to the residue, and the solvent was distilled off under reduced pressure. Ethyl acetate (6.1 mL) was again added to the residue, the solvent was distilled off under reduced pressure, ethyl acetate (54.5 mL) was further added to the residue, the organic layer was washed with a 20 wt % sodium chloride aqueous solution (15.2 mL), a 10 wt % potassium dihydrogenphosphate aqueous solution (15.2 mL) and a 20 wt % sodium chloride aqueous solution (15.2 mL) in that order, and the solvent was distilled off under reduced pressure. Ethyl acetate (6.1 mL) was added to the resultant residue, the insoluble matter was removed by filtration, and the solvent was distilled off from the filtrate under reduced pressure to obtain an oily product (2.70 g) containing the title compound. The product was used in the subsequent step without further purification.

The $^1$H-NMR spectrum matched that of the title compound obtained in Example 1 (step 3).

Step 4

Synthesis of 3-(3-fluoro-2-aminopyridin-4-ylmethyl)-7-hydroxy-4-methyl-2-oxo-2H-1-benzopyran methanesulfonate

[Chemical Formula 56]

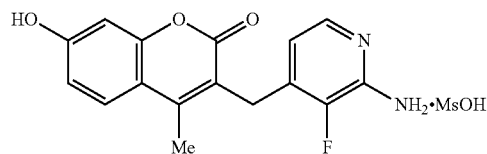

Under a nitrogen atmosphere, the oily product of step 3 (2.70 g) was dissolved in ethyl acetate (5.47 mL), resorcinol (1.32 g, 12.0 mmol) and methanesulfonic acid (8.20 mL, 126 mmol) were added while stirring at room temperature, and after warming to 50° C., the mixture was stirred for 4 hours. The reaction mixture was cooled to room temperature and allowed to stand for 16 hours, water (2.7 mL) was then added, and the mixture was stirred at 80° C. for 7 hours. The reaction mixture was again cooled to room temperature and allowed to stand for 16 hours, and after the mixture was warmed to 70° C., seed crystals (27.4 mg) were added. Water (5.5 mL) was then added, the mixture was stirred for 1 hour, ethanol (13.7 mL) was further added, and the mixture was stirred for 30 minutes. It was then cooled to 25° C., ethanol (38.2 mL) was added, and the mixture was stirred for 30 minutes. The precipitated crystals were collected by filtration, washed twice with ethanol (16.4 mL), and dried under reduced pressure to obtain the title compound (2.20 g).

Yield (overall yield from the 2-acetylamino-5-chloro-3-fluoropyridine used in step 2): 53%

The MS spectrum matched that of the title compound obtained in Example 1 (step 4).

Example 14

Steps 1 and 2

Synthesis of 2-acetylamino-5-chloro-3-fluoro-4-formylpyridine

[Chemical Formula 57]

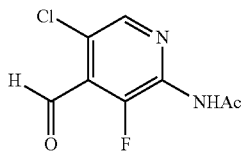

A solid (3.44 g) containing the title compound was obtained in the same manner as steps 1 and 2 of Example 1. The product was used in the subsequent step without further purification.

Step 3

Synthesis of 2-[(2-acetylamino-3-fluoropyridin-4-yl)methyl]-3-oxobutanoic acid ethyl ester

[Chemical Formula 58]

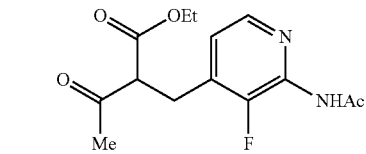

Under a nitrogen atmosphere, water (8.0 mL) was added to the solid product of step 2 (3.44 g), 3-oxobutanoic acid (1.35 g, 10.4 mmol), ethylenediamine diacetate (852 mg, 4.73 mmol), toluene (10.0 mL) and ethyl acetate (6.0 mL) were further added while stirring, and after warming to 40° C., the mixture was stirred for 5 hours. The reaction mixture was cooled to room temperature, the organic layer was separated, and 2-propanol (3.0 mL) was added to a portion (4.18 g) of the organic layer (16.70 g). 20% Pd(OH)$_2$ carbon (383 mg; water content: 46.2%) and a solution of triethylamine (5.07 g, 50.1 mmol) and formic acid (1.87 g, 40.6 mmol) in 2-propanol (2.7 mL) were further added in that order while stirring, and after warming to 50° C., the mixture was stirred for 2 hours. The reaction mixture was filtered through celite, and the residue was washed with 2-propanol (7.6 mL) The filtrate and wash solution (21.7 g) were combined, the solvent was distilled off under reduced pressure, ethyl acetate (1.5 mL) was added to the residue, and the solvent was distilled off under reduced pressure. Ethyl acetate (13.7 mL) was again added to the residue, the organic layer was washed with a 20 wt % sodium chloride aqueous solution (3.8 mL), a 10 wt % potassium dihydrogenphosphate aqueous solution (3.8 mL) and a 20 wt % sodium chloride aqueous solution (3.8 mL) in that order, and the solvent was distilled off under reduced pressure to obtain an oily product (655 mg) containing the title compound.

The $^1$H-NMR spectrum matched that of the title compound obtained in Example 1 (step 3).

The invention claimed is:

1. A method for producing a compound represented by formula (VI):

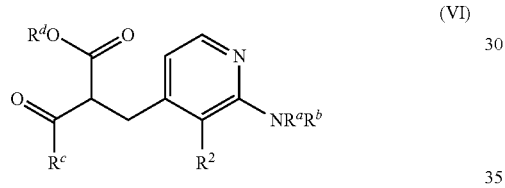

(VI)

wherein $R^2$ represents a hydrogen atom or a halogen atom, $R^a$ and $R^b$ each independently represents a hydrogen atom or an amino protecting group, or $R^a$ and $R^b$ taken together represent an amino protecting group, and $R^c$ and $R^d$ each independently represents a C$_{1-6}$ alkyl group, the method comprising the following steps A to D:

Step A:

a step in which $R^a R^b$NH, wherein $R^a$ and $R^b$ each independently represents a hydrogen atom or an amino protecting group, or $R^a$ and $R^b$ taken together represent an amino protecting group, reacts with a compound represented by formula (I):

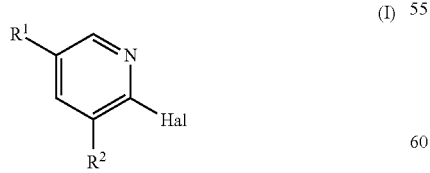

(I)

wherein $R^1$ and $R^2$ each independently represents a hydrogen atom or a halogen atom, and Hal represents a halogen atom, to obtain a compound represented by formula (II):

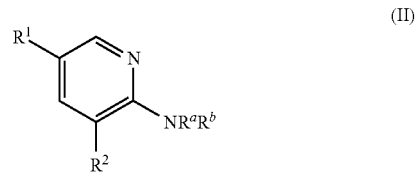

(II)

wherein $R^1$ and $R^2$ each independently represents a hydrogen atom or a halogen atom, and $R^a$ and $R^b$ each independently represents a hydrogen atom or an amino protecting group, or $R^a$ and $R^b$ taken together represent an amino protecting group;

Step B:

a step in which the compound represented by formula (II) reacts with a base and a formylating agent to obtain a compound represented by formula (III):

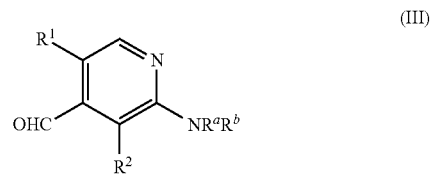

(III)

wherein $R^1$ and $R^2$ each independently represents a hydrogen atom or a halogen atom, and $R^a$ and $R^b$ each independently represents a hydrogen atom or an amino protecting group, or $R^a$ and $R^b$ taken together represent an amino protecting group;

Step C:

a step in which the compound represented by formula (III) reacts with a compound represented by formula (IV):

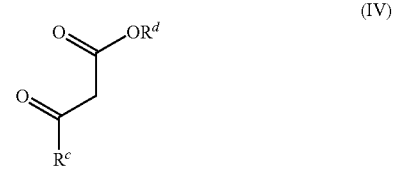

(IV)

wherein $R^c$ and $R^d$ each independently represents a C$_{1-6}$ alkyl group, to obtain a compound represented by formula (V):

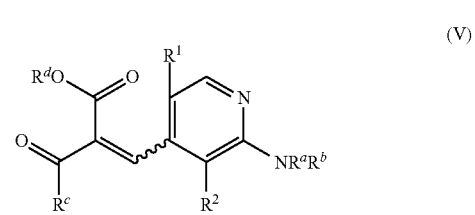

(V)

wherein $R^1$ and $R^2$ each independently represents a hydrogen atom or a halogen atom, $R^a$ and $R^b$ each independently represents a hydrogen atom or an amino protecting group, or $R^a$ and $R^b$ taken together represent an amino protecting group, and $R^c$ and $R^d$ each independently represents a $C_{1-6}$ alkyl group;

Step D:

a step in which the compound represented by formula (V) is subjected to
(a) reduction of double bond when $R^1$ is a hydrogen atom, or
(b) reduction of double bond and hydrogenolysis of $R^1$ when $R^1$ is a halogen atom, to obtain a compound represented by formula (VI):

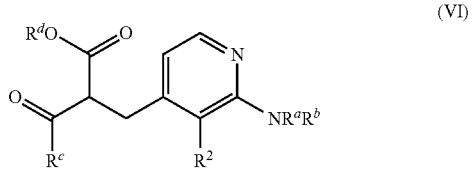

(VI)

wherein $R^2$ represents a hydrogen atom or a halogen atom, $R^a$ and $R^b$ each independently represents a hydrogen atom or an amino protecting group, or $R^a$ and $R^b$ taken together represent an amino protecting group, and $R^c$ and $R^d$ each independently represents a $C_{1-6}$ alkyl group.

2. The method according to claim 1, wherein $R^a R^b NH$ is acetamide ($H_3CCONH_2$).

3. The method according to claim 1, wherein $R^1$ is a chlorine atom, and the combination of the base and the formylating agent in step B is a combination of lithium hexamethyldisilazide and N,N-dimethylformamide or a combination of lithium hexamethyldisilazide and 4-formylmorpholine.

4. The method according to claim 1, wherein the reaction of the compound represented by formula (III) with the compound represented by formula (IV) in step C is performed in the presence of a base and an acid.

5. The method according to claim 1, wherein the reaction solvent in step C is a mixed solvent of water, an acetate ester solvent and an aromatic hydrocarbon solvent.

6. The method according to claim 1, wherein the reaction solvent in step D is a mixed solvent of an acetate ester solvent, an aromatic hydrocarbon solvent and an alcohol solvent.

7. The method according to claim 1, wherein the reaction solvent in step C or step D is 2,2,2-trifluoroethanol.

8. The method according to claim 1, wherein the reaction (a) or (b) in step D is performed using triethylamine, formic acid and carbon-supported palladium.

9. The method according to claim 1, wherein the compound represented by formula (VI) is a compound of the formula:

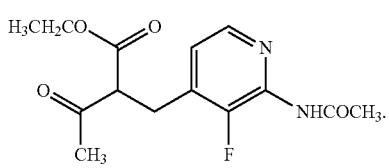

10. The method according to claim 1, wherein the compound represented by formula (I) is a compound of the formula:

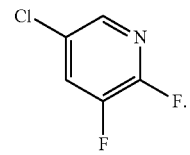

11. A method for producing a compound represented by formula (VII):

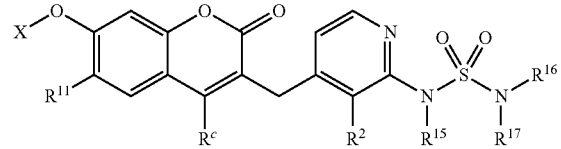

(VII)

wherein $R^2$ represents a hydrogen atom or a halogen atom, $R^c$ represents $C_{1-6}$ alkyl group, X represents a heteroaryl group or $R^{13}R^{14}NCO-$, $R^{11}$ represents a hydrogen atom, a halogen atom, a cyano group, a $C_{1-6}$ alkyl group, a $C_{2-7}$ alkenyl group, a carbamoyl group or a $C_{2-7}$ alkynyl group where the $C_{2-7}$ alkynyl group may optionally be substituted with a $C_{1-4}$ acyl group, $R^{13}$, $R^{14}$, $R^{16}$ and $R^{17}$ each independently represents a hydrogen atom, a $C_{1-6}$ alkoxy group, a $C_{3-8}$ cycloalkyl group or a $C_{1-6}$ alkyl group where the $C_{1-6}$ alkyl group may optionally be substituted with a cyano group, a halogen atom, a hydroxy group, a $C_{1-6}$ alkoxy group or $-NR^{23}R^{24}$, or the combination of $R^{13}$ and $R^{14}$ and the combination of $R^{16}$ and $R^{17}$ may each independently, together with the nitrogen atom to which they are bonded, optionally form a 4- to 6-membered heterocyclic group having at least one nitrogen atom, and $R^{15}$, $R^{23}$ and $R^{24}$ each independently represents a hydrogen atom or a $C_{1-6}$ alkyl group, or a pharmaceutically acceptable salt thereof, wherein the method comprises the following steps A to G:

Step A:

a step in which $R^a R^b NH$, wherein $R^a$ and $R^b$ each independently represents a hydrogen atom or an amino protecting group, or $R^a$ and $R^b$ taken together represent an amino protecting group, reacts with a compound represented by formula (I):

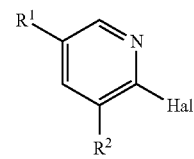

(I)

wherein $R^1$ and $R^2$ each independently represents a hydrogen atom or a halogen atom, and Hal represents a halogen atom, to obtain a compound represented by formula (II):

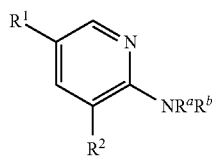

(II)

wherein
$R^1$ and $R^2$ each independently represents a hydrogen atom or a halogen atom, and
$R^a$ and $R^b$ each independently represents a hydrogen atom or an amino protecting group, or $R^a$ and $R^b$ taken together represent an amino protecting group;

Step B:
a step in which the compound represented by formula (II) reacts with a base and a formylating agent to obtain a compound represented by formula (III):

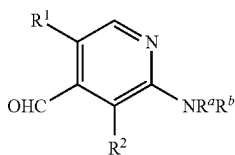

(III)

wherein
$R^1$ and $R^2$ each independently represents a hydrogen atom or a halogen atom, and
$R^a$ and $R^b$ each independently represents a hydrogen atom or an amino protecting group, or $R^a$ and $R^b$ taken together represent an amino protecting group;

Step C:
a step in which the compound represented by formula (III) reacts with a compound represented by formula (IV):

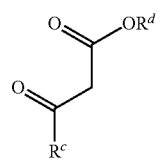

(IV)

wherein $R^c$ and $R^d$ each independently represents a $C_{1-6}$ alkyl group,
to obtain a compound represented by formula (V):

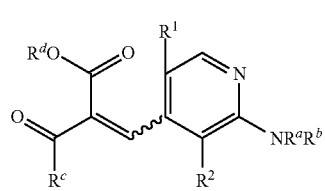

(V)

wherein
$R^1$ and $R^2$ each independently represents a hydrogen atom or a halogen atom, $R^a$ and $R^b$ each independently represents a hydrogen atom or an amino protecting group, or $R^a$ and $R^b$ taken together represent an amino protecting group, and
$R^c$ and $R^d$ each independently represents a $C_{1-6}$ alkyl group;

Step D:
a step in which the compound represented by formula (V) is subjected to
(a) reduction of double bond when $R^1$ is a hydrogen atom, or
(b) reduction of double bond and hydrogenolysis of $R^1$ when $R^1$ is a halogen atom,
to obtain a compound represented by formula (VI):

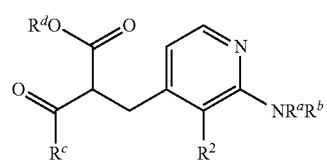

(VI)

wherein
$R^2$ represents a hydrogen atom or a halogen atom,
$R^a$ and $R^b$ each independently represents a hydrogen atom or an amino protecting group, or $R^a$ and $R^b$ taken together represent an amino protecting group, and
$R^c$ and $R^d$ each independently represents a $C_{1-6}$ alkyl group;

Step E:
a step in which the compound represented by formula (VI) reacts with a compound represented by formula (VIII):

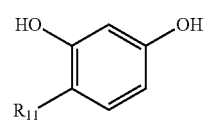

(VIII)

wherein $R^{11}$ represents a hydrogen atom, a halogen atom, a cyano group, a $C_{1-6}$ alkyl group, a $C_{2-7}$ alkenyl group, a carbamoyl group or a $C_{2-7}$ alkynyl group where the $C_{2-7}$ alkynyl group may optionally be substituted with a $C_{1-4}$ acyl group,
in the presence of an acid to obtain a compound represented by formula (IX):

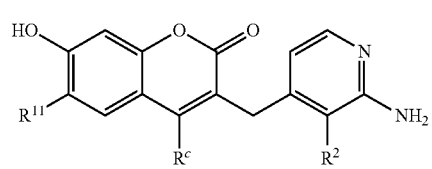

(IX)

wherein
$R^2$ represents a hydrogen atom or a halogen atom,
$R^c$ represents a $C_{1-6}$ alkyl group, and
$R^{11}$ represents a hydrogen atom, a halogen atom, a cyano group, a $C_{1-6}$ alkyl group, a $C_{2-7}$ alkenyl group, a carbamoyl group or a $C_{2-7}$ alkynyl group where the $C_{2-7}$ alkynyl group may optionally be substituted with a $C_{1-4}$ acyl group, or a pharmaceutically acceptable salt or acid adduct thereof;

Step F:
a step in which the compound represented by formula (IX) or the pharmaceutically acceptable salt or acid adduct thereof reacts with X—Y wherein
X represents a heteroaryl group or $R^{13}R^{14}NCO-$,
Y represents a halogen atom,
$R^{13}$ and $R^{14}$ each independently represents a hydrogen atom, a $C_{1-6}$ alkoxy group, a $C_{3-8}$ cycloalkyl group or a $C_{1-6}$ alkyl group where the $C_{1-6}$ alkyl group may optionally be substituted with a cyano group, a halogen atom, a hydroxy group, a $C_{1-6}$ alkoxy group or $-NR^{23}R^{24}$, or the combination of $R^{13}$ and $R^{14}$ may together with the nitrogen atom to which they are bonded, optionally form a 4- to 6-membered heterocyclic group having at least one nitrogen atom, and
$R^{23}$ and $R^{24}$ each independently represents a hydrogen atom or a $C_{1-6}$ alkyl group,
in the presence of a base to obtain a compound represented by formula (X):

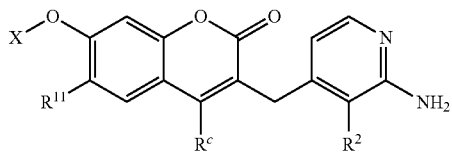

(X)

wherein
$R^2$ represents a hydrogen atom or a halogen atom,
$R^c$ represents a $C_{1-6}$ alkyl group,
X represents a heteroaryl group or $R^{13}R^{14}NCO-$,
$R^{11}$ represents a hydrogen atom, a halogen atom, a cyano group, a $C_{1-6}$ alkyl group, a $C_{2-7}$ alkenyl group, a carbamoyl group or a $C_{2-7}$ alkynyl group where the $C_{2-7}$ alkynyl group may optionally be substituted with a $C_{1-4}$ acyl group,
$R^{13}$ and $R^{14}$ each independently represents a hydrogen atom, a $C_{1-6}$ alkoxy group, a $C_{3-8}$ cycloalkyl group or a $C_{1-6}$ alkyl group where the $C_{1-6}$ alkyl group may optionally be substituted with a cyano group, a halogen atom, a hydroxy group, a $C_{1-6}$ alkoxy group or $-NR^{23}R^{24}$, or the combination of $R^{13}$ and $R^{14}$ may together with the nitrogen atom to which they are bonded, optionally form a 4- to 6-membered heterocyclic group having at least one nitrogen atom, and
$R^{23}$ and $R^{24}$ each independently represents a hydrogen atom or a $C_{1-6}$ alkyl group;

Step G:
a step in which the compound represented by formula (X) reacts with a compound represented by formula (XI):

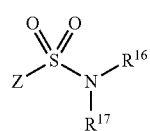

(XI)

wherein
Z represents a leaving group,
$R^{16}$ and $R^{17}$ each independently represents a hydrogen atom, a $C_{1-6}$ alkoxy group, a $C_{3-8}$ cycloalkyl group or a $C_{1-6}$ alkyl group where the $C_{1-6}$ alkyl group may optionally be substituted with a cyano group, a halogen atom, a hydroxy group, a $C_{1-6}$ alkoxy group or $-NR^{23}R^{24}$, or the combination of $R^{16}$ and $R^{17}$ may together with the nitrogen atom to which they are bonded, optionally form a 4- to 6-membered heterocyclic group having at least one nitrogen atom, and
$R^{23}$ and $R^{24}$ each independently represents a hydrogen atom or a $C_{1-6}$ alkyl group,
to obtain a compound represented by formula (VII'):

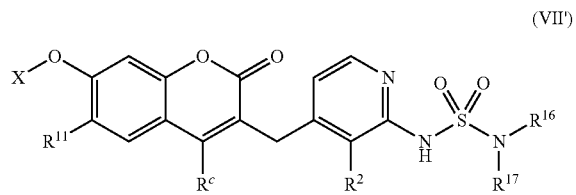

(VII')

wherein
$R^2$ represents a hydrogen atom or a halogen atom,
$R^c$ represents $C_{1-6}$ alkyl group,
X represents a heteroaryl group or $R^{13}R^{14}NCO-$,
$R^{11}$ represents a hydrogen atom, a halogen atom, a cyano group, a $C_{1-6}$ alkyl group, a $C_{2-7}$ alkenyl group, a carbamoyl group or a $C_{2-7}$ alkynyl group where the $C_{2-7}$ alkynyl group may optionally be substituted with a $C_{1-4}$ acyl group,
$R^{13}$, $R^{14}$, $R^{16}$ and $R^{17}$ each independently represents a hydrogen atom, a $C_{1-6}$ alkoxy group, a $C_{3-8}$ cycloalkyl group or a $C_{1-6}$ alkyl group where the $C_{1-6}$ alkyl group may optionally be substituted with a cyano group, a halogen atom, a hydroxy group, a $C_{1-6}$ alkoxy group or $-NR^{23}R^{24}$, or the combination of $R^{13}$ and $R^{14}$ and the combination of $R^{16}$ and $R^{17}$ may each independently, together with the nitrogen atom to which they are bonded, optionally form a 4- to 6-membered heterocyclic group having at least one nitrogen atom, and
$R^{23}$ and $R^{24}$ each independently represents a hydrogen atom or a $C_{1-6}$ alkyl group.

12. The method according to claim 11, wherein the compound represented by formula (VII) or the pharmaceutically acceptable salt thereof is a potassium salt of a compound of the formula:

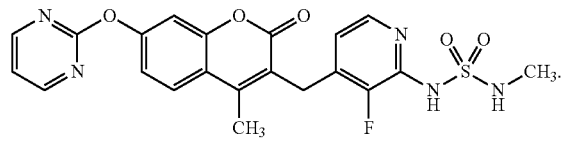 [SMILES: CNS(=O)(=O)Nc1nccc(Cc2c(C)c3ccc(Oc4ncccn4)cc3oc2=O)c1F]

* * * * *